US011273270B2

United States Patent
Kleyman et al.

(10) Patent No.: US 11,273,270 B2
(45) Date of Patent: Mar. 15, 2022

(54) SURGICAL GAS DELIVERY SYSTEM WITH REMOTE GASEOUS SEALING MODULE AND GAS SEALED SLEEVE FOR ACCESSING A SURGICAL CAVITY

(71) Applicant: Conmed Corporation, Utica, NY (US)

(72) Inventors: Gennady Kleyman, Brooklyn, NY (US); Michael J. Augelli, Prospect, CT (US); Mikiya Silver, New Haven, CT (US)

(73) Assignee: Conmed Corporation, Utica, NY (US)

( * ) Notice: Subject to any disclaimer, the term of this patent is extended or adjusted under 35 U.S.C. 154(b) by 321 days.

(21) Appl. No.: 16/015,438

(22) Filed: Jun. 22, 2018

(65) Prior Publication Data

US 2019/0388629 A1 Dec. 26, 2019

(51) Int. Cl.
*A61M 13/00* (2006.01)
*A61B 17/00* (2006.01)
*A61B 17/34* (2006.01)

(52) U.S. Cl.
CPC ..... *A61M 13/006* (2014.02); *A61B 17/00234* (2013.01); *A61B 17/3423* (2013.01); *A61B 17/3462* (2013.01); *A61B 17/3474* (2013.01); *A61B 2017/3419* (2013.01); *A61B 2217/005* (2013.01); *A61M 2205/125* (2013.01)

(58) Field of Classification Search
CPC .. A61M 13/006; A61M 13/00; A61M 13/003; A61M 39/02; A61M 2039/027; A61M 2039/0279; A61M 2039/0646; A61M 2202/02; A61M 2205/07; A61M 2205/3344; A61B 17/3423; A61B 17/3462; A61B 2017/3419; A61B 17/00234; A61B 17/3474; A61B 2217/005; A61B 17/3417; A61B 17/34; A61B 17/3415; A61B 2017/3445
See application file for complete search history.

(56) References Cited

U.S. PATENT DOCUMENTS

| 7,854,724 | B2 | 12/2010 | Stearns et al. |
| 8,715,219 | B2 | 5/2014 | Stearns et al. |
| 8,795,223 | B2 | 8/2014 | Stearns et al. |
| 8,961,451 | B2 | 2/2015 | Stearns et al. |
| 9,295,490 | B2 | 3/2016 | Stearns et al. |
| 9,375,539 | B2 | 6/2016 | Stearns et al. |

(Continued)

OTHER PUBLICATIONS

International Search Report and Written Opinion issued in corresponding PCT Application No. PCT/US2019/035709 dated Oct. 1, 2019.

*Primary Examiner* — Amber R Stiles
*Assistant Examiner* — Avery Smale
(74) *Attorney, Agent, or Firm* — Locke Lord LLP; Scott D. Wofsy

(57) ABSTRACT

A system for performing an endoscopic surgical procedure in a surgical cavity of a patient that includes a gas delivery device configured to deliver a flow of pressurized gas to a gas delivery lumen extending therefrom, a gaseous sealing module communicating with a distal end of the gas delivery lumen and configured to generate a gaseous seal within a gas sealed lumen extending therefrom, and an access port communicating with a distal end of the gas sealed lumen so as to provide sealed instrument access to the surgical cavity and maintain a stable pressure within the surgical cavity.

8 Claims, 20 Drawing Sheets

(56) References Cited

U.S. PATENT DOCUMENTS

| | | | |
|---|---|---|---|
| 9,387,295 B1 | 7/2016 | Mastri et al. | |
| 9,387,296 B1 | 7/2016 | Mastri et al. | |
| 9,526,849 B2 | 12/2016 | Stearns et al. | |
| 9,907,569 B2 | 3/2018 | Stearns et al. | |
| 2007/0088275 A1* | 4/2007 | Stearns | A61B 17/3423 604/164.01 |
| 2007/0249990 A1 | 10/2007 | Cosmescu | |
| 2014/0074015 A1* | 3/2014 | Mastri | A61B 17/3417 604/26 |
| 2014/0180198 A1* | 6/2014 | Ott | A61B 17/3474 604/24 |
| 2016/0287817 A1* | 10/2016 | Mastri | A61M 5/165 |
| 2017/0100160 A1 | 4/2017 | Sawalhe et al. | |
| 2017/0156755 A1 | 6/2017 | Poll et al. | |
| 2017/0361084 A1 | 12/2017 | Zergiebel et al. | |
| 2018/0133416 A1 | 5/2018 | Silver et al. | |

* cited by examiner

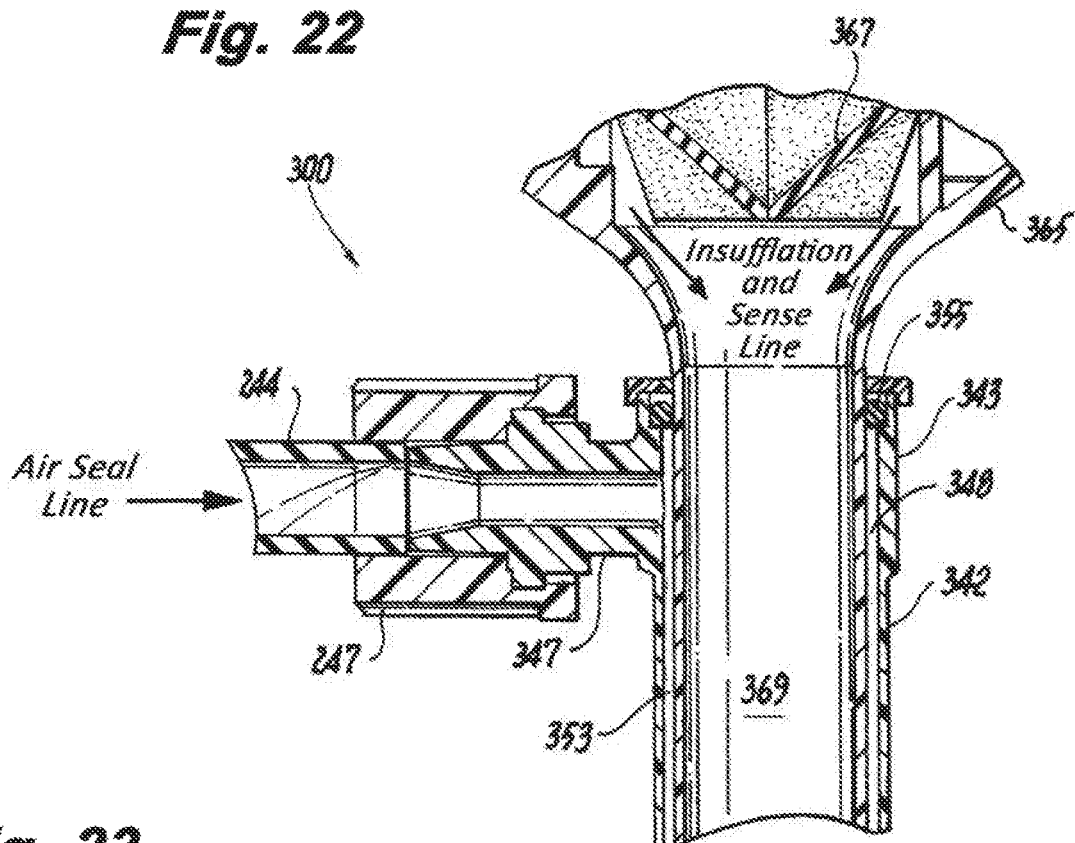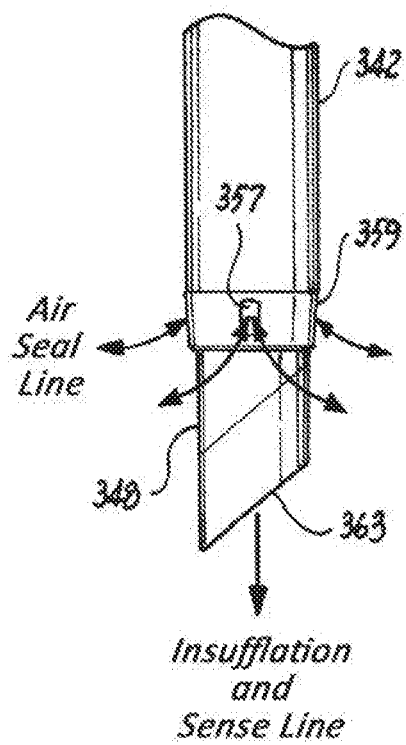

SURGICAL GAS DELIVERY SYSTEM WITH REMOTE GASEOUS SEALING MODULE AND GAS SEALED SLEEVE FOR ACCESSING A SURGICAL CAVITY

BACKGROUND OF THE INVENTION

1. Field of the Invention

The subject invention is directed to endoscopic surgery, and more particularly, to a surgical gas delivery device for use in endoscopic surgical procedures that includes an internal or remote gaseous sealing module for generating a gaseous seal within a lumen extending therefrom that communicates with a mechanically sealed surgical access port to maintain stable pressure within a surgical cavity.

2. Description of Related Art

The use of pneumatically sealed surgical access devices or trocars, such as those that have been disclosed in commonly assigned U.S. Pat. Nos. 7,854,724 and 8,795,223, in combination with a multi-modal gas delivery device, such as those that have been disclosed in commonly assigned U.S. Pat. Nos. 8,715,219; 8,961,451; 9,295,490 and 9,375,539 have been demonstrated to have numerous advantages. These advantages include valve-less access to a surgical cavity (e.g., the abdominal or thoracic cavity), facilitation of smoke evacuation, and stable maintenance of pressure within the surgical cavity, as well as several medical and clinical benefits.

The combination of these devices form a surgical system that relies on the presence of an annular jet assembly housed within the trocar for receiving pressurized gas from the gas delivery device to generate a gaseous sealing zone within the body of the trocar. That annular jet assembly is disclosed in commonly assigned U.S. Pat. No. 9,907,569, and it is designed to provide a static mechanism akin to a nozzle that funnels down pressurized gas into a narrower passage that increases the velocity of the gas in order to generate the gaseous sealing zone.

In commonly assigned U.S. Pat. Nos. 9,387,295 and 9,387,296, as well as in commonly assigned U.S. Application Publication No. 2016/0287817, it was proposed to move the location of the annular jet assembly (or a similar nozzle design) from the trocar device and into the filter cartridge housing of a related filtered tube set configured for operative associate with the gas delivery device. This enabled the use of more conventional commercially available access devices instead of the pneumatically sealed trocars described above.

It has now been determined that further advantages can be achieved by moving the location of the annular jet assembly (or a similar nozzle design) into the tubing of a filtered tube set or into the housing of a multi-modal gas delivery device itself. This would enable the technology to be compatible with a multitude of new proprietary and commercially-available end effectors and access devices. Indeed, in certain surgical scenarios, it may be required that all of the access ports used in a procedure be of one variety. For example, these may include robotically assisted surgeries that are only compatible with a certain type or brand of reusable cannulas.

Another advantage of the gas management systems of the subject invention would be market or cost-driven, wherein hospitals have policies to use disposable cannulas of a particular brand (for example due to a financial contract) or reusable cannulas to save money. In these examples, the systems of the subject invention would enable a surgeon to gain pressure-stability and smoke evacuation functionality without the requirement to displace one of their lower-cost access ports.

SUMMARY OF THE DISCLOSURE

The subject invention is directed to a new and useful system for performing an endoscopic surgical procedure in a surgical cavity, which includes a gas delivery device configured to deliver a flow of pressurized gas to a gas delivery lumen extending therefrom, a gaseous sealing module communicating with a distal end of the gas delivery lumen and configured to generate a gaseous seal within a gas sealed lumen extending therefrom, and an access port communicating with a distal end of the gas sealed lumen so as to provide mechanically sealed instrument access to the surgical cavity and maintain a stable pressure within the surgical cavity. The access port includes a valve sealed proximal housing for providing mechanically sealed instrument access to the surgical cavity.

The system further includes a gas return lumen extending from the gaseous sealing module back to the gas delivery device. The gas delivery device includes a pump for delivering pressurized gas to the gas delivery lumen and for suctioning gas from the gas return lumen. The gas delivery lumen and the gas return lumen communicate with a filter assembly that is dimensioned and configured for reception within the gas delivery device.

The system further includes an insufflator within the gas delivery device for delivering insufflation gas to a second access port through an insufflation lumen. The second access port includes a mechanically sealed proximal housing for providing sealed instrument access to the surgical cavity.

Preferably, the gaseous sealing module includes a housing supporting a jet assembly for receiving pressurized gas from the gas delivery lumen to generate the gaseous seal, and wherein gas spent generating the gaseous seal is suctioned through the gas return lumen back to the pump in the gas delivery device. In an embodiment of the subject invention, the gaseous sealing module includes a vented housing for facilitating air entrainment from atmosphere into the surgical cavity and gas release to atmosphere from the surgical cavity. It is envisioned that the gaseous sealing module could also communicate with a bi-directional filtration element to filter entrained air and/or gas released to atmosphere from the surgical cavity.

In one embodiment, the housing of the gaseous sealing module is configured such that the connections for the gas delivery lumen and the gas return lumen are arranged perpendicular to the connection for the gas sealed lumen. In another embodiment, the housing of the gaseous sealing module is configured such that the connection for the gas delivery lumen and the gas return lumen are arranged in-line with the connection for the gas sealed lumen. In yet another embodiment, the housing of the gaseous sealing module is configured such that the connection for the gas delivery lumen and the gas return lumen are arranged in parallel to the connection for the gas sealed lumen.

In these embodiments, it is envisioned that the gas delivery lumen and the gas return lumen could be arranged to interface with the housing of the gaseous sealing module in a parallel configuration or in a concentric configuration. Alternatively, the gaseous sealing module could include a two-part housing assembly having a proximal subassembly connected to the gas delivery lumen and the gas return lumen, and a distal sub-assembly connected to the gas sealed lumen.

The subject invention is also directed to a system for performing an endoscopic surgical procedure in a body cavity, which includes a gas delivery device having a pump for delivering pressurized gas to a gas delivery lumen extending therefrom and having an insufflator for delivering insufflation gas to an insufflation lumen extending therefrom. A gaseous sealing module communicates with a distal end of the gas delivery lumen, external to the gas delivery device, and it is configured to generate a gaseous seal within a gas sealed lumen extending therefrom. A gas sealed sleeve having a proximal end portion communicates with a distal end portion of the gas sealed lumen, and a tubular access port configured for coaxial installation within the gas sealed sleeve and having a valve sealed proximal housing providing mechanically sealed instrument access to the surgical cavity communicates with a distal end of the insufflation lumen.

An annular channel is formed between an inner surface of the sleeve and an outer surface of the access port so that the gas sealed lumen is in communication with the surgical cavity to maintain a stable pressure within the surgical cavity. A sealing ring is associated with the proximal end portion of the gas sealed sleeve for sealing a proximal end of the annular channel, and a plurality of circumferentially spaced apart flow channels are formed in the distal end portion of the gas sealed sleeve to facilitate communication between the annular channel and the surgical cavity. The system further includes a gas return lumen extending from the gaseous sealing module back to the pump in the gas delivery device. The gas delivery lumen and the gas return lumen communicate with a filter assembly that is dimensioned and configured for reception within the gas delivery device.

The subject invention is also directed to a novel method of accessing a surgical cavity of a patient, which includes the steps of: providing a gas sealed sleeve; installing a valve sealed trocar into the gas sealed sleeve; and introducing the gas sealed sleeve together with the installed valve sealed trocar into the surgical cavity of the patient. The method further comprises the steps of connecting the sleeve to a gas sealed lumen adapted for bi-directional gas flow to and from the sleeve, and connecting the trocar to an insufflation and sensing lumen.

The subject invention is also directed to a system for performing an endoscopic surgical procedure in a surgical cavity, which includes a gas delivery device housing a pump configured to deliver pressurized gas to an internal gas delivery lumen extending from the pump. A gaseous sealing module is housed within the gas delivery device, in communication with the gas delivery lumen and configured to generate a gaseous seal within an internal gas sealed tube extending therefrom. The gas sealed tube is adapted and configured to communicate with a gas sealed lumen extending externally from the gas delivery device, and a valve sealed access port communicates with a distal end of the gas sealed lumen so as to provide mechanically sealed instrument access to the surgical cavity and maintain a stable pressure within the surgical cavity.

The system further includes an internal gas return lumen that extends from the gaseous sealing module to recirculate gas used to form the gaseous seal back to the pump within the gas delivery device. The gas delivery device also includes an insufflator for delivering insufflation gas to a second valve sealed access port through an insufflation lumen.

In this embodiment of the subject invention, the gaseous sealing module preferably includes an integral assembly formed by a metallic disk with at least one radially inwardly angled nozzle formed therein for generating the gaseous seal, and a cylindrical bore for accommodating air entrainment into and gas release from the gas sealed lumen.

It is envisioned that the at least one radially inwardly angled nozzle can be radially spaced apart from the cylindrical bore, which could be offset from a central axis of the disk. Alternatively, the disk can have a plurality of radially inwardly angled nozzles formed therein, which would be radially spaced apart from the cylindrical bore, which could be offset from a central axis of the disk. Or, the disk could have a plurality of radially inwardly angled nozzles formed therein, which surround the cylindrical bore, which could be aligned with a central axis of the disk.

The subject invention is also directed to a tube set for use with a gas delivery device for performing an endoscopic surgical procedure in a surgical cavity, which includes a filter cartridge assembly having first and second flow paths formed therein, a first lumen extending from the filter cartridge and communicating with the first flow path for communicating with the surgical cavity to maintain a stable pressure therein and facilitate smoke evacuation, and a second lumen extending from the filter cartridge and communicating with the second flow path to deliver insufflation gas to the surgical cavity and sense cavity pressure.

A fitting is operatively associated with a distal end of the first lumen for connection with a first mechanically sealed access port, and a fitting is operatively associated with a distal end of the second lumen for connection with a second mechanically sealed access port. There may be at least one filter element disposed within the first flow path of the filter cartridge, and/or at least one filter element disposed within the second flow path of the filter cartridge.

These and other features of the gas circulation system and the system of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas circulation system and gas sealed surgical access devices of the subject invention without undue experimentation, preferred embodiments thereof will be described in detail herein below with reference to the figures wherein:

FIG. 22 is a cross-sectional view taken along line 22-22 of FIG. 18;

FIG. 23 is a localized plan view of the distal end portion of the surgical access assembly shown in FIG. 18;

DETAILED DESCRIPTION OF THE PREFERRED EMBODIMENTS

Figure 1:
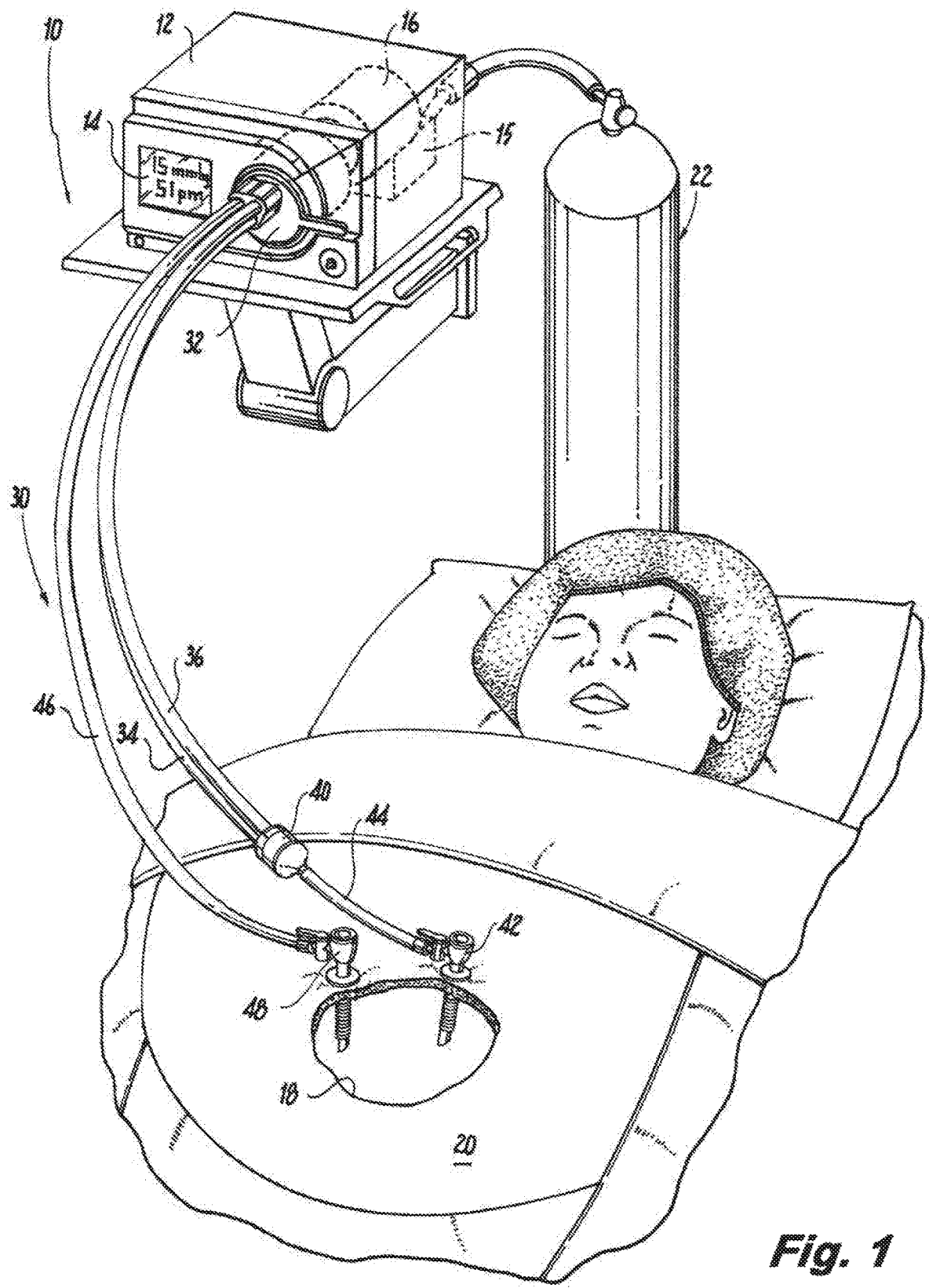
FIG. 1 is an illustration of the gas delivery system of the subject invention during an endoscopic surgical procedure conducted within the abdominal cavity of a patient, wherein the system includes a gas delivery device, gas delivery and return lines extending between the gas delivery device and a remote gaseous sealing module, a first valve sealed access port communicating with the gas sealed lumen attached to the gaseous sealing module, and an insufflation and sensing line extending between the gas delivery device and a second valve sealed access port.

Referring now to the drawings wherein like reference numerals identify similar structural elements and features of the subject invention, there is illustrated in FIG. 1 a gas circulation system for performing an endoscopic surgical procedure in a surgical cavity of a patient, and more particularly, for performing a laparoscopic surgical procedure in the abdominal cavity of a patient, that is constructed in accordance with a preferred embodiment of the subject disclosure and is designated generally by reference numeral 10. Those skilled in the art will readily appreciate that the gas circulation system 10 of the subject invention can be used for performing thoracoscopic surgical procedures in the thoracic cavity of a patient, as well as, the performance of endo-luminal surgical procedures, such as trans-anal and trans-esophageal surgical procedures.

Referring to FIG. 1, the gas circulation system 10 of the subject invention is specifically designed to cooperate with a programmable multi-modal gas delivery device 12. The gas delivery device 12 is of the type described, for example, in commonly assigned U.S. Pat. No. 9,375,539, the disclosure of which is herein incorporated by reference in its entirety. The gas delivery device 12 includes a graphical user interface 14 for setting operating parameters and a pump 16 for facilitating the circulation/recirculation of pressurized gas relative to the surgical cavity 18 of a patient 20. The gas delivery device 12 is connected to a portable source of surgical gas 22 for delivering insufflation gas to the surgical cavity 18 of the patient 20 by way of an internal insufflator 15. Alternatively, gas could be supplied to the gas delivery device 12 from a permanent source.

Figure 2:
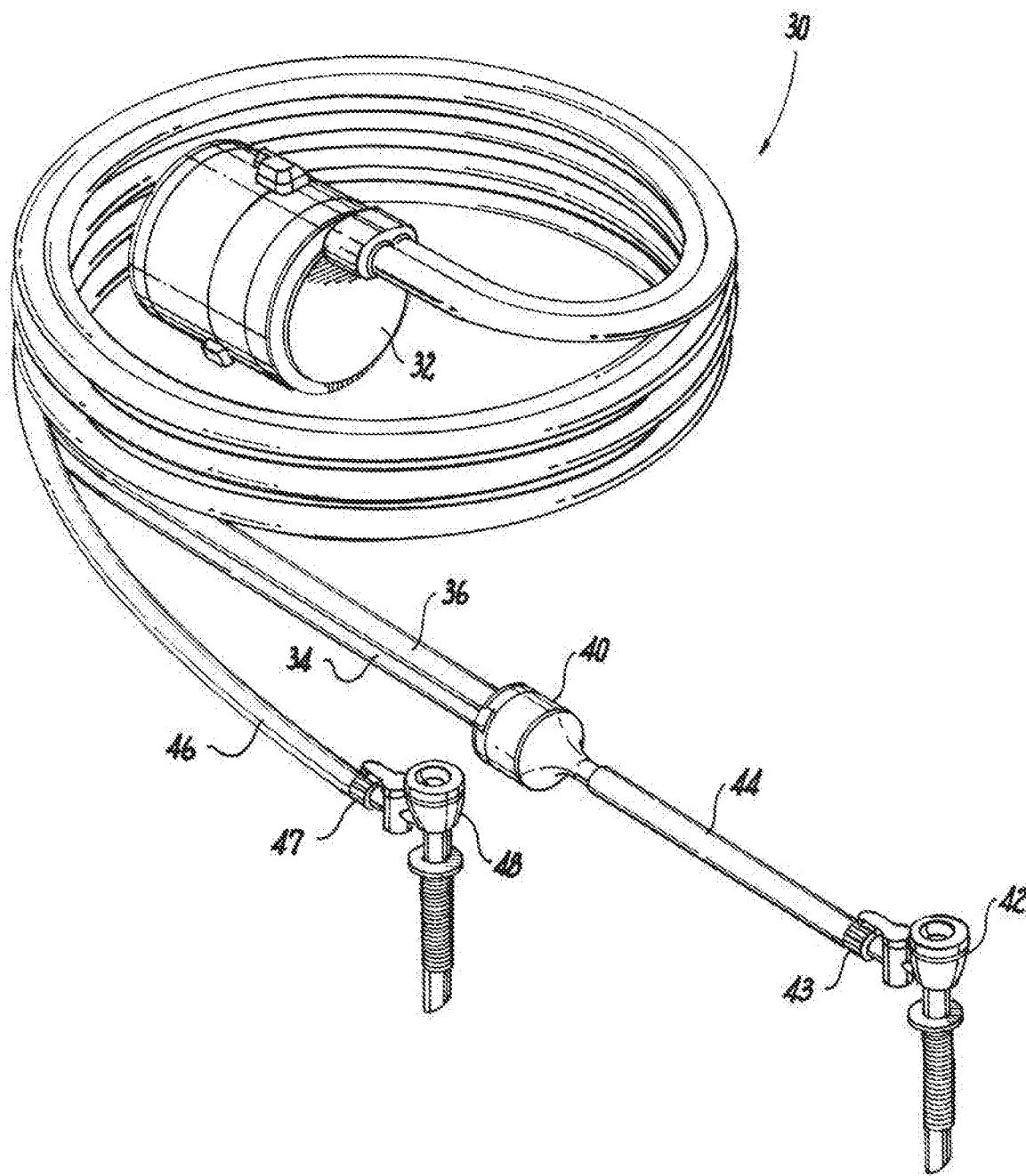
FIG. 2 is a perspective view of the filtered tube set, remote gaseous sealing module and valve sealed access ports of the gas delivery system illustrated in FIG. 1.

With continuing reference to FIG. 1 in conjunction with FIG. 2, the system 10 further includes a filtered tube set 30 that is operatively associated with the gas delivery device 12. The filtered tube set 30 includes a disposable filter cartridge 32 of the type described in commonly assigned U.S. Pat. No. 9,526,849, the disclosure of which is herein incorporated by reference in its entirety. A gas delivery lumen 34 and a gas return lumen 36 extend between the filter cartridge 32 and a remotely located gaseous sealing module 40, which will be described in more detail below. A first valve sealed access port 42 communicates with the gaseous sealing module 40 through a gas sealed lumen 44, and an insufflation and sensing line 46 extends between the filter cartridge 32 and a second valve sealed access port 48. A connector 43 is associated with a distal end of the gas sealed lumen 44 for mating with a fitting on the first access port 42, and a connector 47 is associated with a distal end of the insufflation and sensing line 46 for mating with a fitting on the second access port 48.

Figure 3:
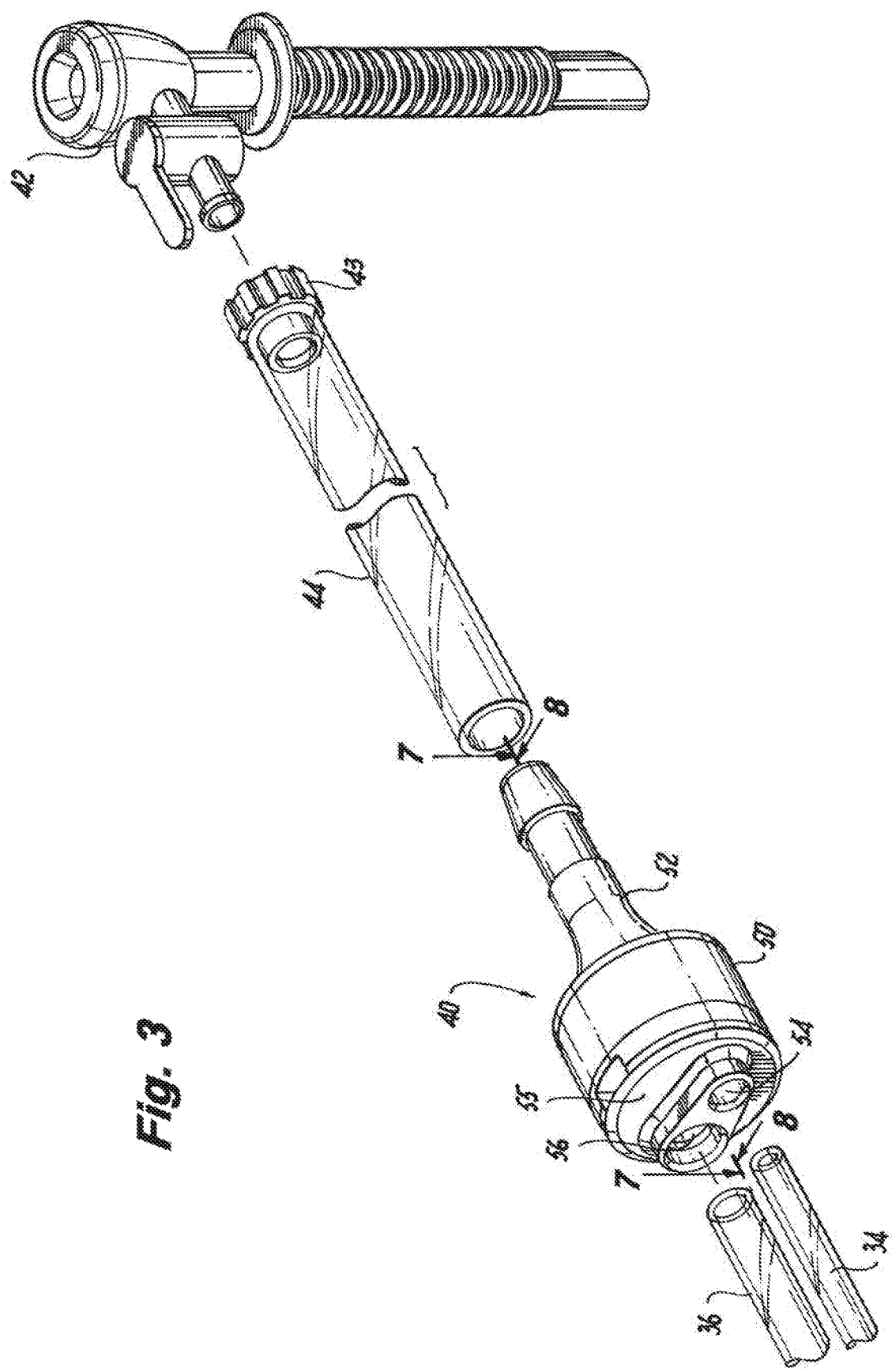
FIG. 3 is an exploded perspective view of a portion of the gas delivery system of FIG. 1, illustrating the connections between the gas delivery and return lines, the remote gaseous sealing module, the gas sealed lumen, and the first valve sealed access port.

Referring now to FIG. 3, the remote gaseous sealing module 40 (i.e., located remote from the access port 42 and from the gas delivery device 12) is shown in conjunction with the gas delivery and return lumen 34 and 36, the gas sealed lumen 44 and the first valve sealed access port 42. In general, the remote gaseous sealing module 40 is adapted and configured to generate a gaseous seal which extends through the gas sealed lumen 44 to the first valve sealed access port 42 so as to maintain a stable pressure and facilitate smoke evacuation within the surgical cavity 18 of patient 20 during an endoscopic surgical procedure.

Figure 4:
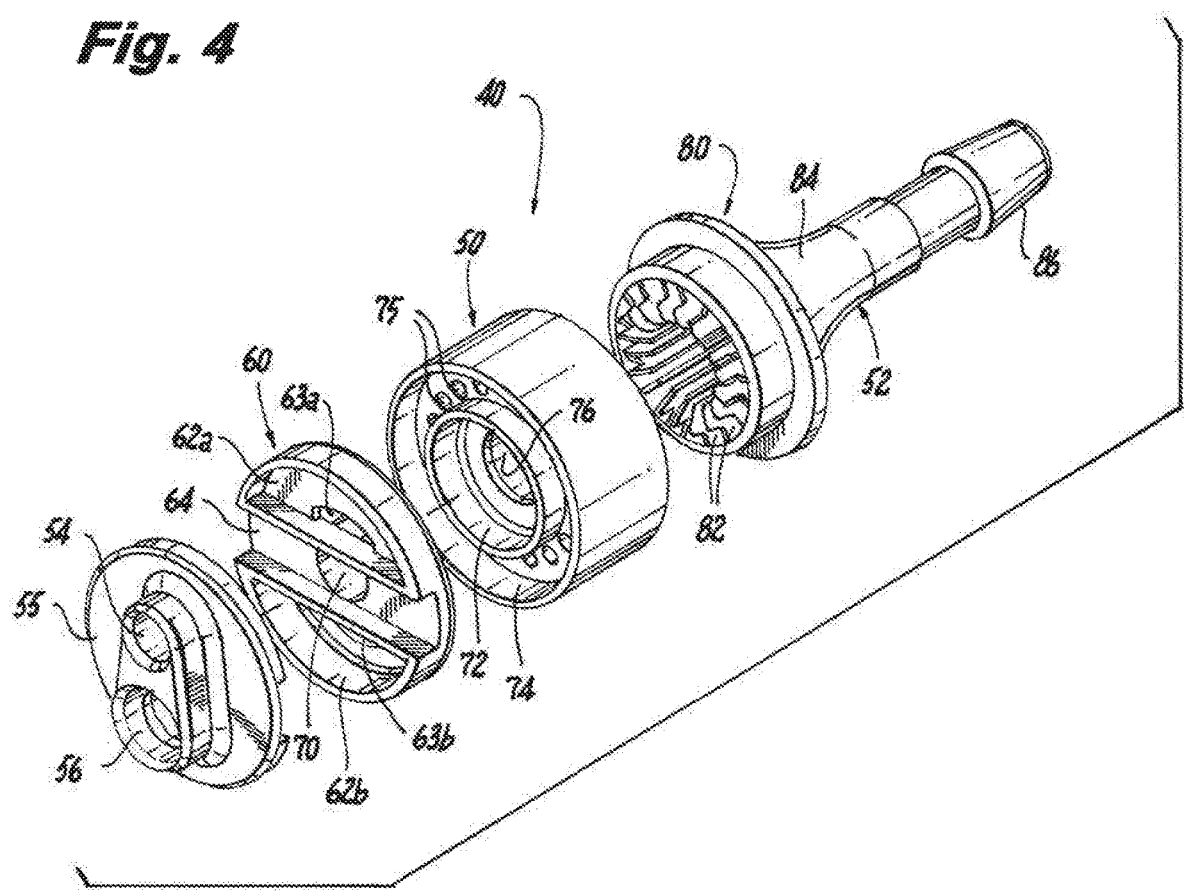
FIG. 4 is an exploded perspective view of the gaseous sealing module of the gas delivery system shown in FIG. 1, with parts separated for ease of illustration.

Referring to FIG. 4, the remote gaseous sealing module 40 includes a generally cylindrical proximal housing portion 50 and an elongated tubular stem portion 52 that extends axially from the proximal housing portion 50. The proximal housing portion 50 is associated with an end cap 55 having an axially offset inlet port 54 for communication with the gas delivery lumen 34 and an adjacent axially offset outlet port 56 for communication with the gas return lumen 36.

Figure 5:
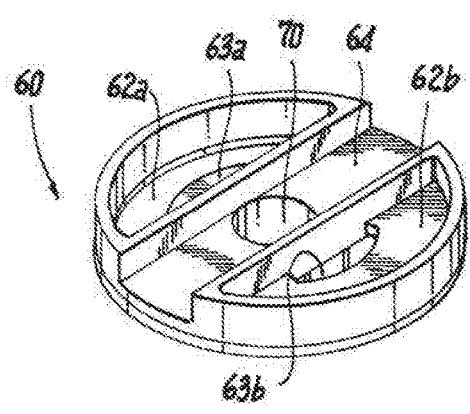
FIGS. 5 and 6 are top and bottom perspective views of the nozzle tube element that forms part of the gaseous sealing module shown in FIG. 4.
Figure 6:
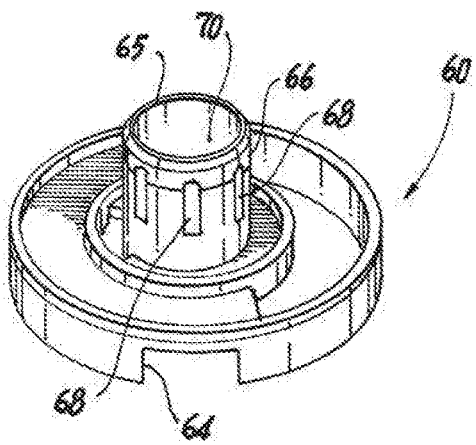

With continuing reference to FIG. 4 in conjunction with FIGS. 5 and 6, the gaseous sealing module 40 further includes a nozzle body 60 sandwiched between the proximal housing portion 50 and the end cap 55, which defines crescent shaped inlet plenum 62a for transmitting pressurized gas from the pump 16 of the gas delivery device 12 through the gas delivery lumen 34 and inlet 54 in end cap 55 for use in generating a gaseous seal within the gaseous sealing module 40, and crescent shaped outlet plenum 62b for receiving spent gas used to form the gaseous seal within the gaseous sealing module 40 through outlet 56 for return to the pump 16 via gas return lumen 36. The crescent shaped plenums 62a and 62b have respective crescent shaped gas conduit channels 63a and 63b.

The nozzle body 60 of gaseous sealing module 40 further includes a central gas transfer plenum 64, which is open to atmosphere at both ends, and is located between the inlet plenums 62a and 62b. Nozzle body 60 also includes a distally extending nozzle tube 65 that communicates with the gas transfer plenum 64. The nozzle tube 65 has a central bore 70 that communicates with the gas transfer plenum 64 to define a bi-directional vent path that facilitates gas exchange to and from the gas sealed gas sealed lumen 44, including but not limited to, air entrainment from atmosphere into the surgical cavity 18 and gas release to atmosphere from the surgical cavity 18 to relieve overpressure. The outer periphery of nozzle tube 65 includes a plurality of circumferentially spaced apart land areas 66, which define a set of circumferentially spaced apart recessed gas jets 68 for accelerating pressurized gas delivered to the gaseous sealing module 40 from gas delivery lumen 34 to form a gaseous seal within the gas sealed lumen 44.

Figure 7:
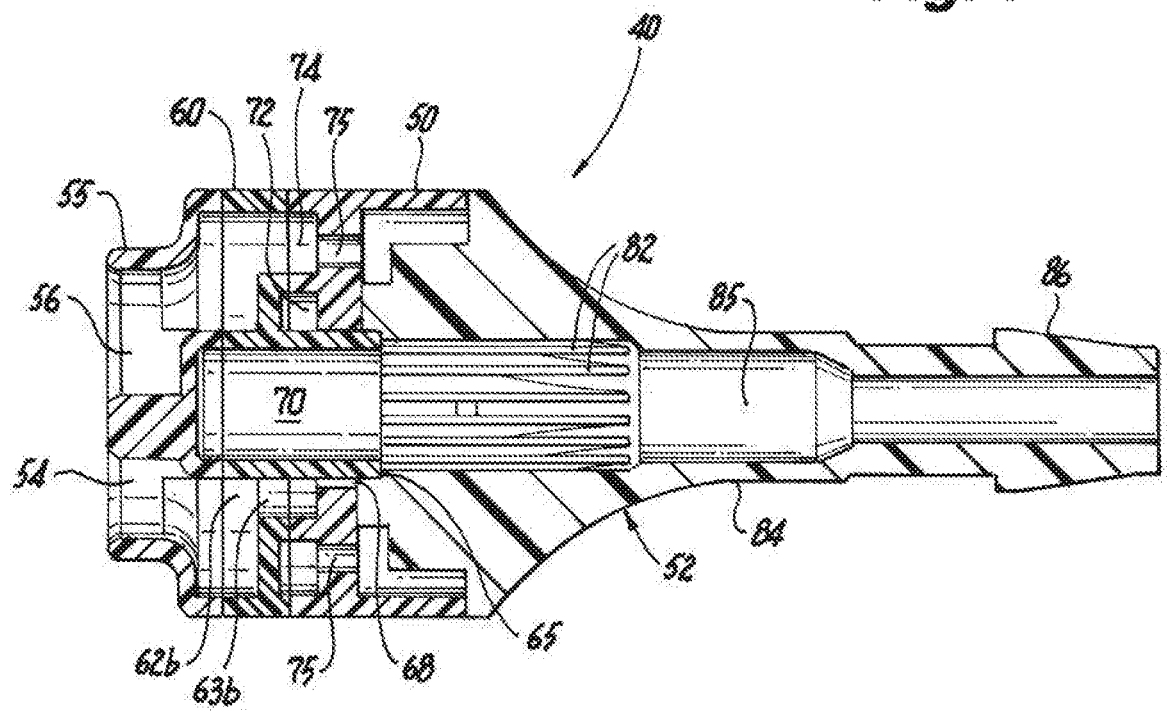
FIGS. 7 and 8 are cross-sectional views of the gaseous sealing module taken along lines 7-7 and 8-8 of FIG. 3.
Figure 8:
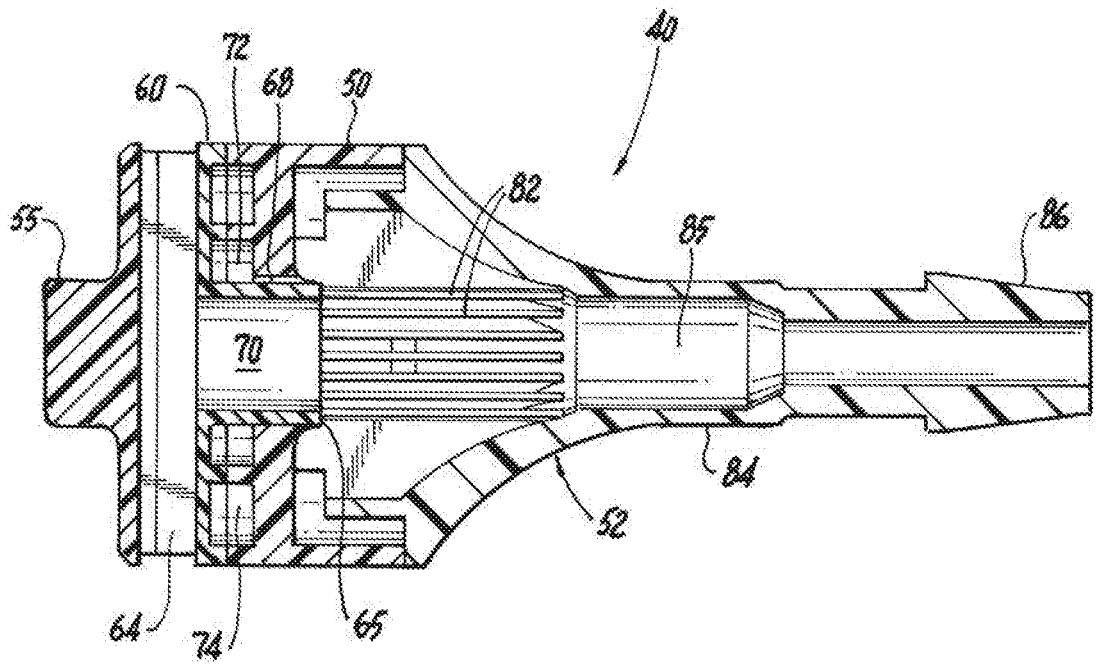
Figure 9:
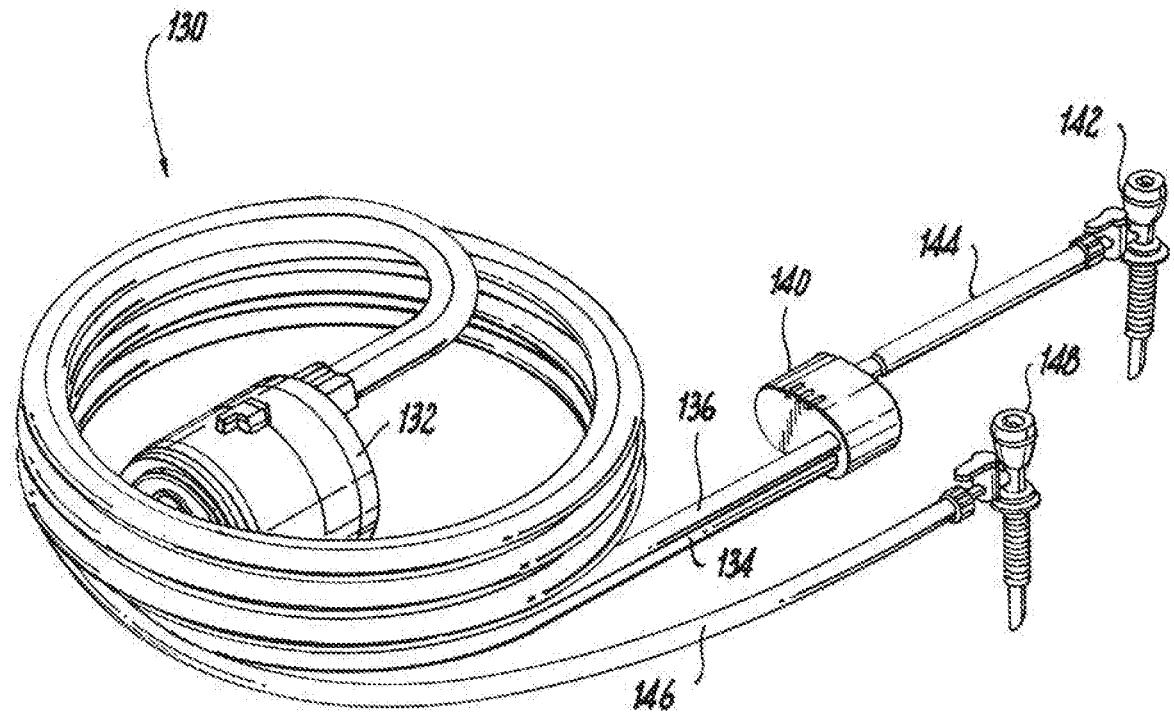
FIG. 9 is an illustration of another embodiment of a filtered tube set for use with the gas delivery device shown in FIG. 1, which includes gas delivery and return lines extending between a filter cartridge configured for reception in the gas delivery device, a remote gaseous sealing module having a two-part housing, a valve sealed access port communicating with the gas sealed lumen attached to the gaseous sealing module and an insufflation and sensing lumen communicating with another valve sealed access port.

With continuing reference to FIG. 4 in conjunction with FIGS. 7 and 8, the proximal housing portion 50 of gaseous sealing module 40 includes a central cylindrical plenum area 72 in communication with the gas inlet channels 63a of the inlet plenum 62a of nozzle body 60, and a surrounding annular plenum area 74 in communication with the gas return channel 63b of the gas return plenum 62b. The annular plenum area 74 includes a plurality of circumferentially spaced apart gas return ports 75.

A nozzle bore 76 is formed within the central plenum area 72, and as best seen in FIGS. 7 and 8, the nozzle tube 65 of nozzle body 60 is dimensioned and configured for engagement within the nozzle bore 76 to form the radially outer boundaries of the circumferentially spaced apart jets 68 recessed into the outer peripheral surface of nozzle tube 65, as described above.

Referring to FIG. 4 in conjunction with FIGS. 7 and 8, the elongated tubular stem portion 52 that extends axially from the proximal housing portion 50 of gaseous sealing module 40 includes a proximal flange portion 80 that houses a plurality of circumferentially spaced apart fins 82 configured to guide spent gas used to generate the gaseous seal back to the annular plenum area 74 by way of the gas return ports 75. The tubular stem portion 52 further includes a medial throat section 84, which defines the interior zone 85 of the gaseous sealing module 40 wherein the gaseous seal is generated by the circumferentially spaced apart jets 68. The stem portion 52 also includes a distal tube fitting 86 which is dimensioned and configured to connect with the gas sealed lumen 44, as best seen in FIG. 3.

Referring now to FIGS. 9 through 12, there is illustrated another filtered tube set constructed in accordance with a preferred embodiment of the subject invention, which is designated generally by reference numeral 130 and it includes a remote gas sealing module 140 that differs from the remote sealing module 40 described above, in that the gas sealed delivery and return lumens are offset from and parallel to the gas sealed lumen.

More particularly, tube set 130 includes a filter cartridge 132, a gas delivery lumen 134 and gas return lumen 136 extending between the filter cartridge 132 and the gaseous sealing module 140, a gas sealed lumen 144 extending from the gaseous sealing module 140 to a first valve sealed access port 142, and an insufflation and sensing lumen 146 extending from the filter cartridge 132 to a second valve sealed access port 148. In this embodiment of the invention, the gaseous sealing module 140 is configured such that the connection for the gas delivery lumen 134 and the gas return lumen 136 are arranged parallel to and offset from the connection for the gas sealed lumen 144.

Figure 11:
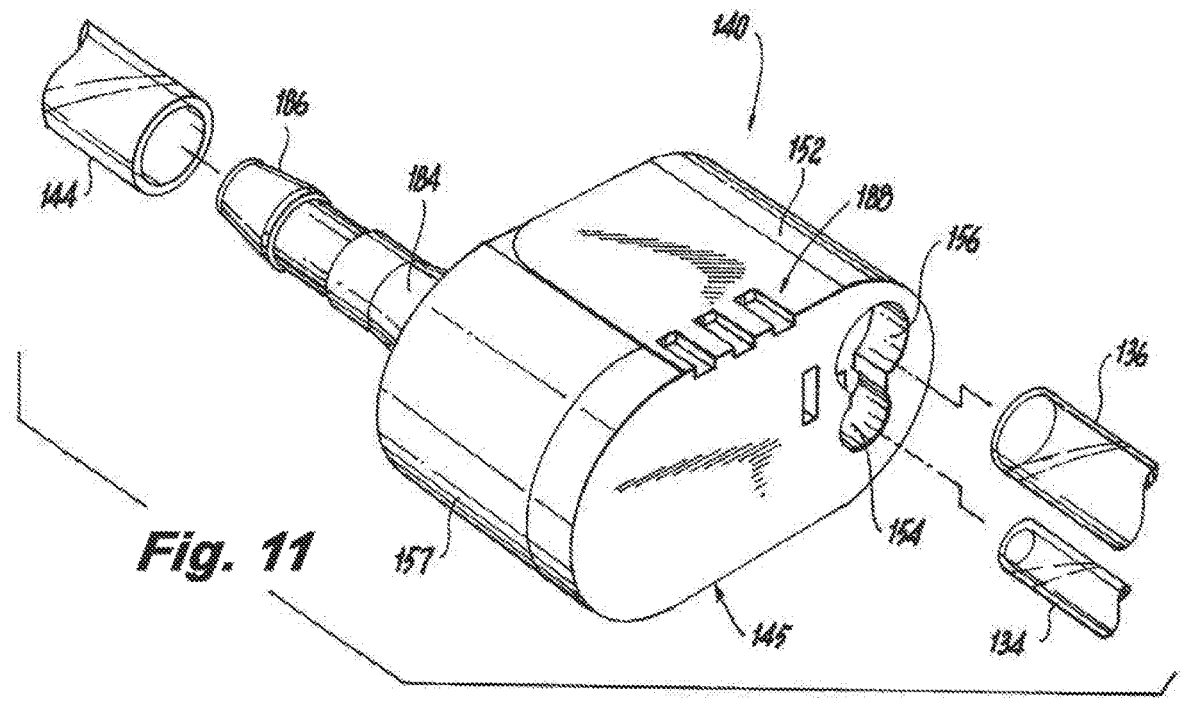
FIG. 11 is an enlarged perspective view of the remote gaseous sealing module shown in FIG. 9.
Figure 12:
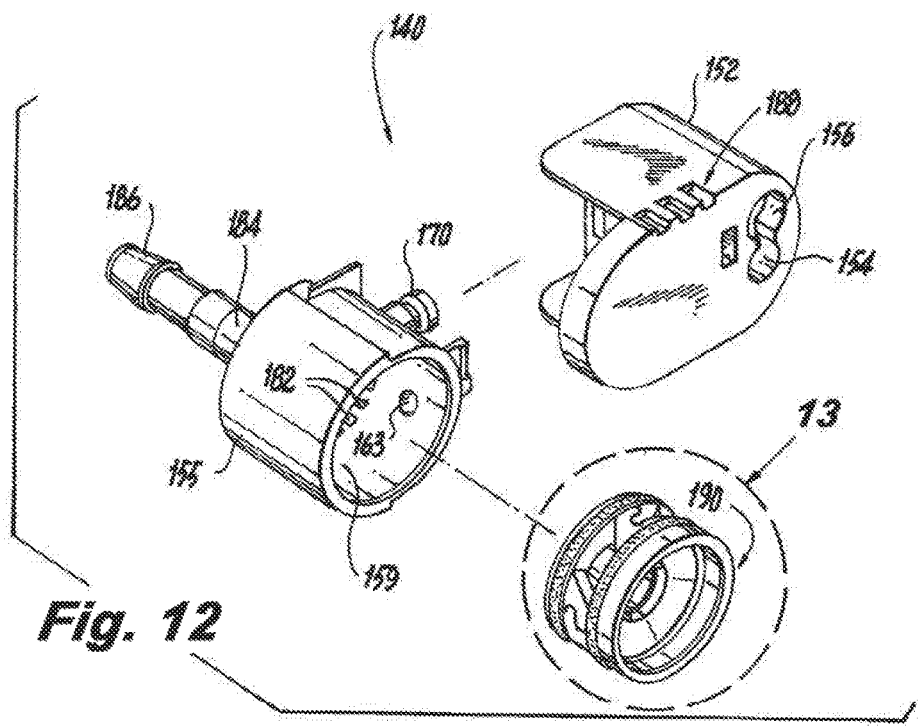
FIG. 12 is an exploded perspective view of the remote gaseous sealing module shown in FIG. 9, with parts separated for ease of illustration, including the annular jet assembly for generating a gaseous seal in the gas sealed lumen extending therefrom.

Referring now to FIGS. 11 and 12, the remote gaseous sealing module 140 includes a two-part mechanically interconnected housing assembly 145 consisting of a first component 152 and a sub-assembly 157. The first component 152 is connected to and communicates with the gas delivery lumen 134 and gas return lumen 136. Sub-assembly 157 is connected to and communicates with the gas sealed lumen 144.

More particularly, component 152 of the two-part housing 145 has an inlet port 154 for direct communication with the gas delivery lumen 134 and an adjacent outlet port 156 for direct communication with the gas return lumen 136. Sub-assembly 157 of the two-part housing 145 includes a body portion 155 defining an interior plenum chamber 159 and a distally extending tube fitting 186 which is dimensioned and configured to connect with the gas sealed lumen 144.

Figure 13:
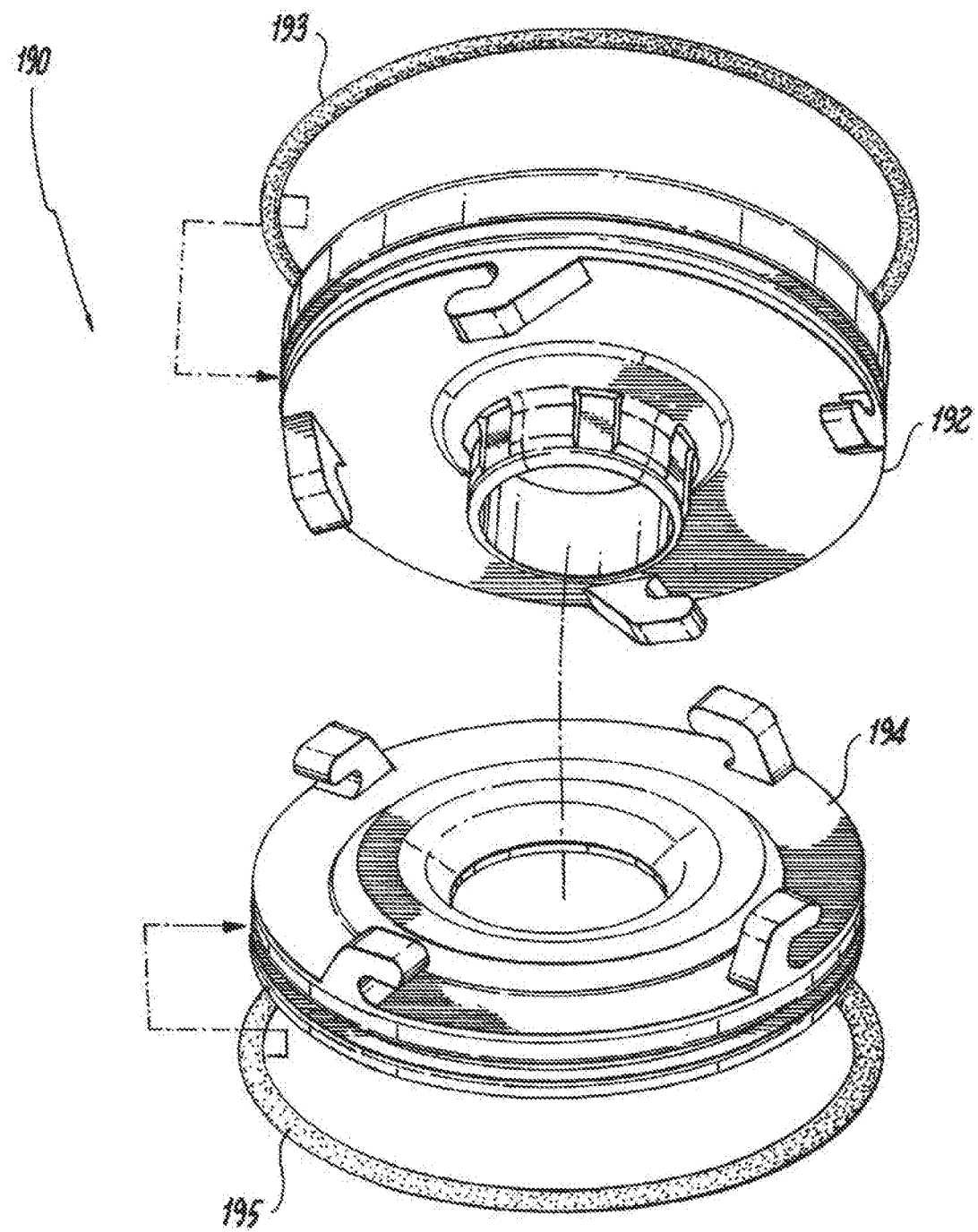
FIG. 13 is an exploded perspective view of the annular jet assembly housed within the gaseous sealing module of FIG. 12.

The interior plenum chamber 159 of body portion 155 is dimensioned and configured to receive a two-part ring jet assembly 190 of the type illustrated in FIG. 13, which is described in more detail in commonly assigned U.S. Pat. No. 9,907,569, the disclosure of which is incorporated herein by reference in its entirety. In general, as shown in FIG. 13, the two-part ring jet assembly 190 is comprised of an upper member 192 with an O-ring seal 193 and a lower ring member 194 with an O-ring seal 195.

Figure 10:
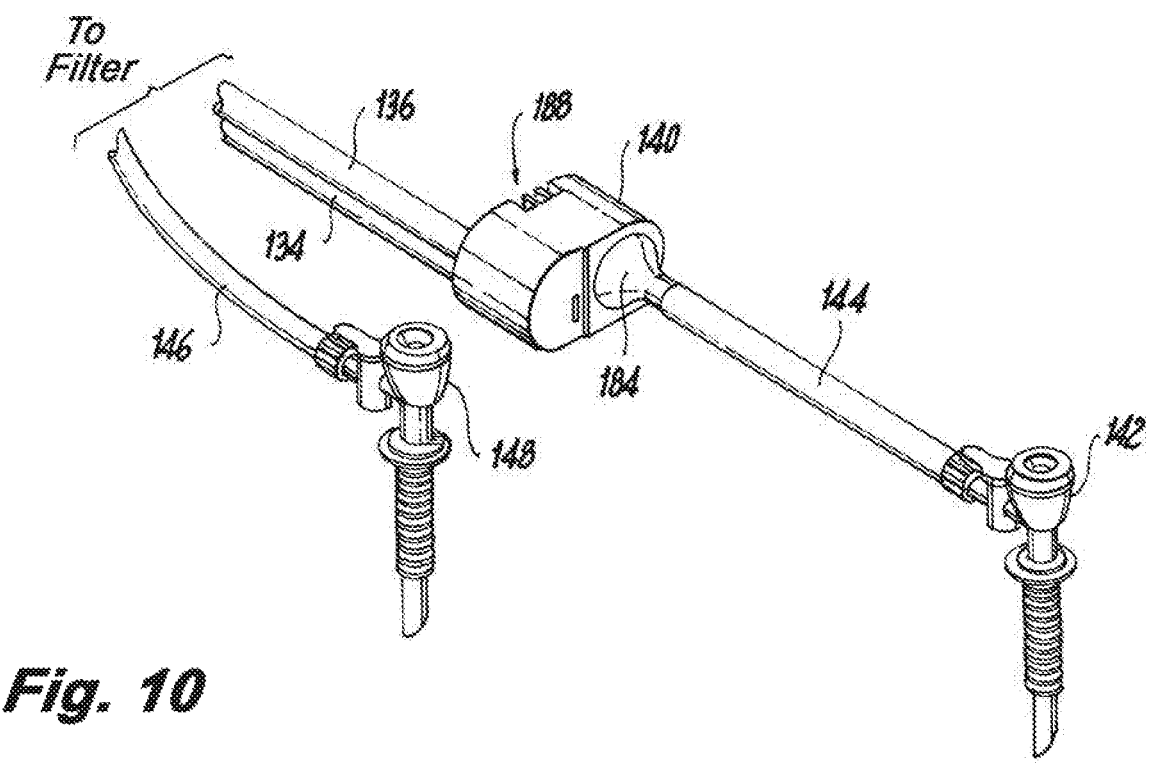
FIG. 10 is an enlarged perspective view of a portion of the gas delivery system of FIG. 9, illustrating and the gas sealed lumen extending between the gaseous sealing module and a first valve sealed access port, and the insufflation and sensing lumen and second valve sealed access port.

The jet assembly 190 receives pressurized gas through an inlet port 163 from the gas delivery lumen 134, and it functions to accelerate that gas so as to generate a gaseous seal within the distal throat area 184 of body portion 155 (see FIG. 10). The gaseous seal that is generated in the throat area 184 creates a stable pressure barrier that maintains stable pressure through the length of the gas sealed lumen 144 to access port 142 so as to maintain a stable pressure and facilitate smoke evacuation within the surgical cavity 18 of a patient 20 during an endoscopic surgical procedure.

As best seen in FIG. 12, circumferentially spaced apart guide fins 182 are provided within the plenum chamber 159 of body portion 155 for guiding the gas spent generating the gaseous seal within throat area 184 back to the gas return lumen 136 by way of an outlet fitting 170. Component 152 also includes a vent path 188 that facilitate gas exchange to and from the gas sealed lumen 144, including but not limited to, air entrainment from atmosphere into the surgical cavity 18 and gas release to atmosphere from the surgical cavity 18 to relieve overpressure.

Referring now to FIGS. 14 through 17, there is illustrated yet another filtered tube set constructed in accordance with a preferred embodiment of the subject invention, which is designated generally by reference numeral 230 and it includes a remote gas sealing module 240 that differs from each of the remote sealing modules described above. More particularly, tube set 230 includes a filter cartridge 232, a gas delivery lumen 234 and gas return lumen 236 extending between the filter cartridge 232 and the gaseous sealing module 240, a gas sealed lumen 244 extending from the gaseous sealing module 240 to a first valve sealed access port 242 and an insufflation and sensing lumen 246 extending from the filter cartridge 232 to a second valve sealed access port 248.

In this embodiment of the invention, the gaseous sealing module 240 is configured such that the gas delivery lumen 234 and the gas return lumen 236 are arranged perpendicular to the output for the gas sealed lumen 244, and the gas delivery lumen 234 and gas return lumen 236 are arranged to interface with the housing 250 of the gaseous sealing module 240 in a concentric configuration.

Figure 15:
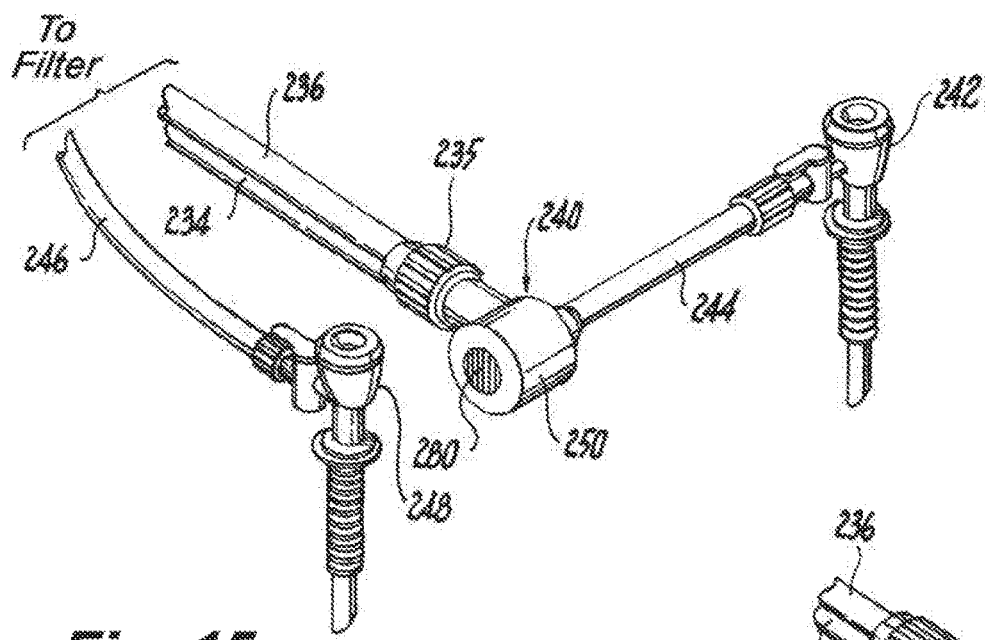
FIG. 15 is an enlarged perspective view of a portion of the gas delivery system of FIG. 14, illustrating and the gas sealed lumen extending between the gaseous sealing module and a first valve sealed access port, and the insufflation lumen and sensing lumen and second valve sealed access port.
Figure 15A:
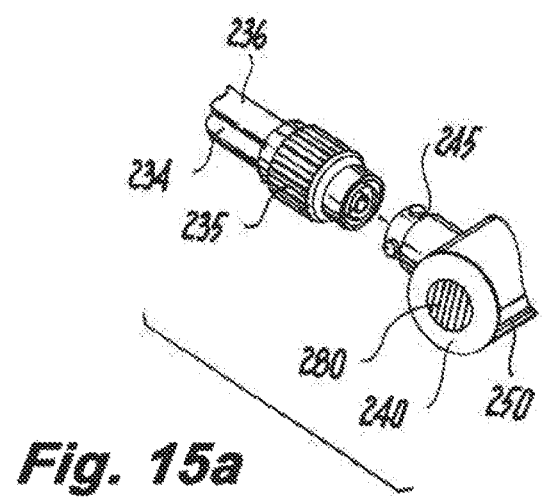
FIG. 15a is a localized view of the connector for the gas delivery and return lines disconnected from the fitting on the gaseous sealing module.
Figure 16:
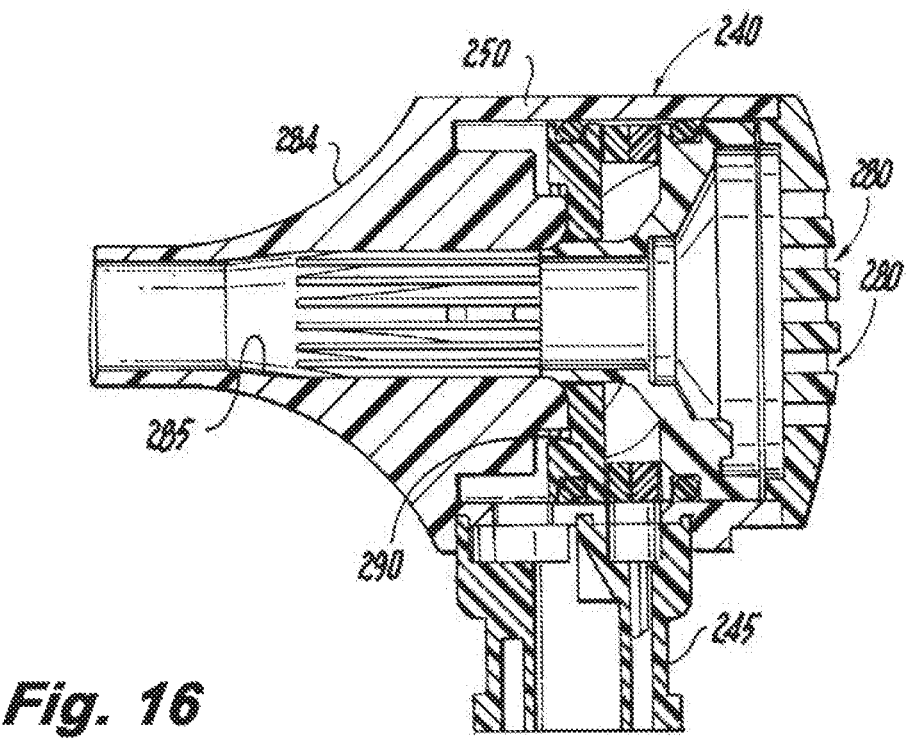
FIGS. 16 and 17 are cross-sectional view taken along line 16-16 of FIG. 15 illustrating the interior of the remote gaseous sealing module and the connection point of the gas delivery and the gas return lumens.
Figure 17:
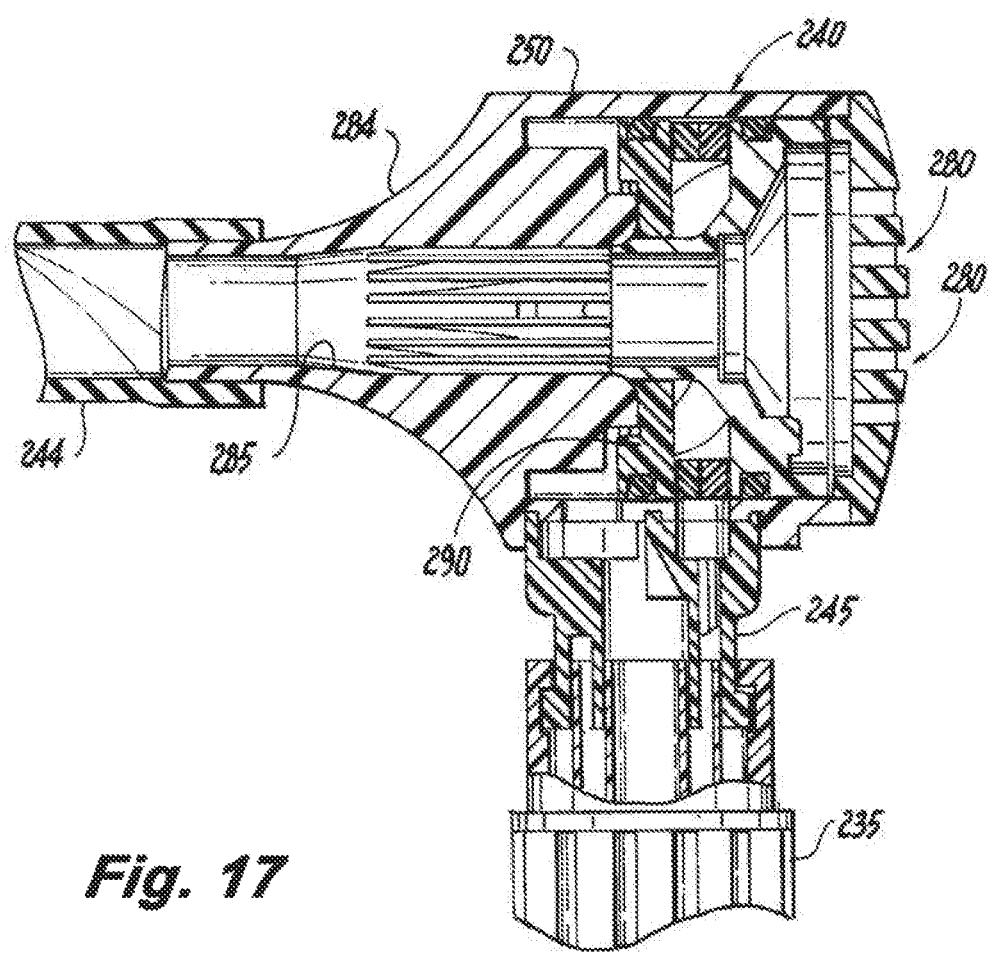
Figure 18:
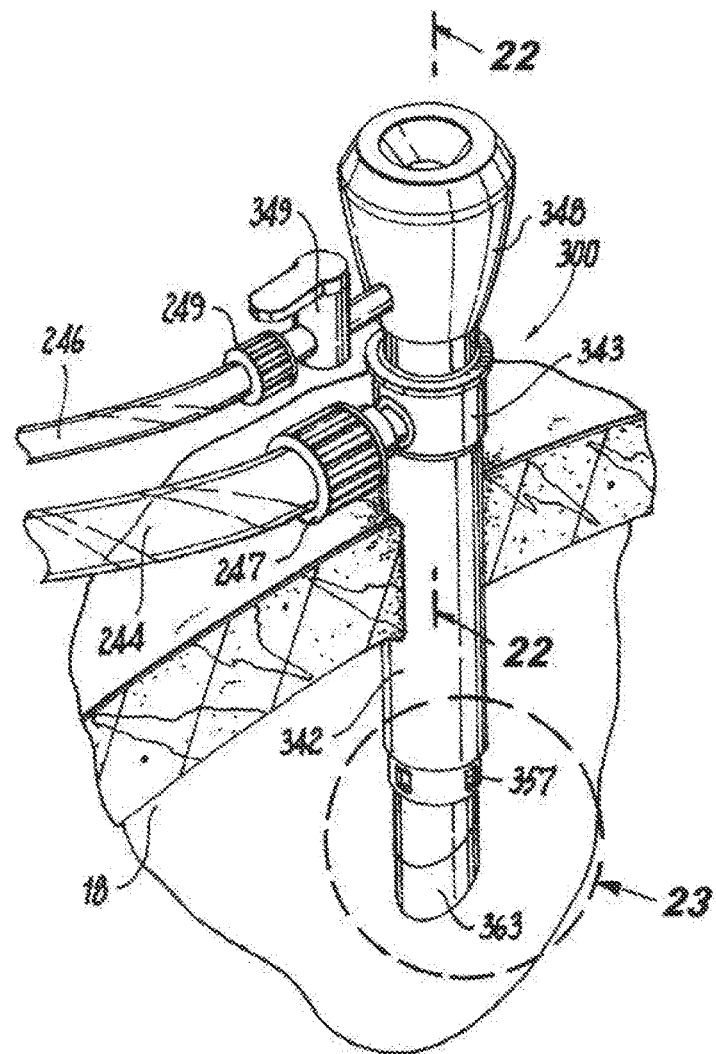
FIG. 18 is a perspective view a surgical access assembly constructed in accordance with a preferred embodiment of the subject invention that includes a gas sealed sleeve having a proximal end portion that communicates with a distal end portion of a gas sealed lumen, and a valve sealed tubular access port configured for coaxial reception within the sleeve.
Figure 19:
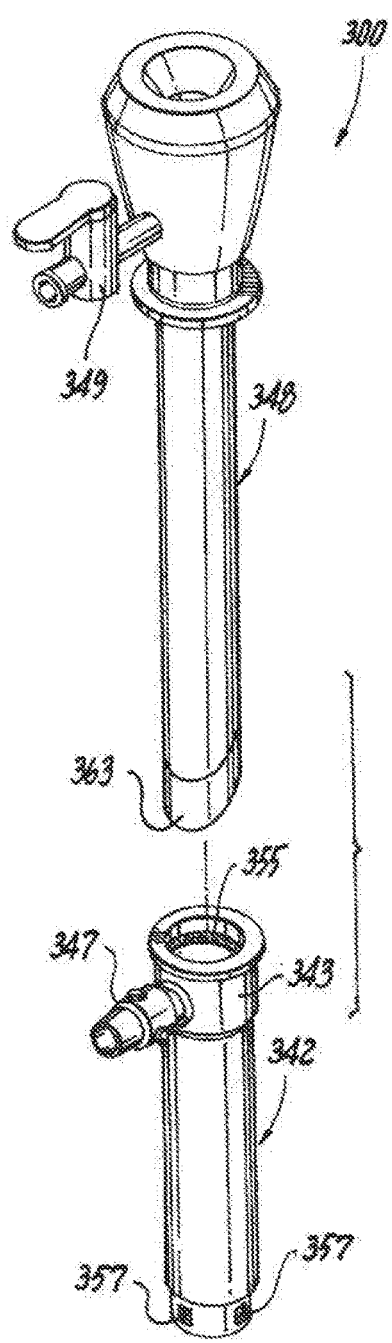
FIG. 19 is an exploded perspective view of the surgical access assembly shown in FIG. 18, with the valve sealed tubular access port separated from the gas sealed sleeve.
Figure 20:
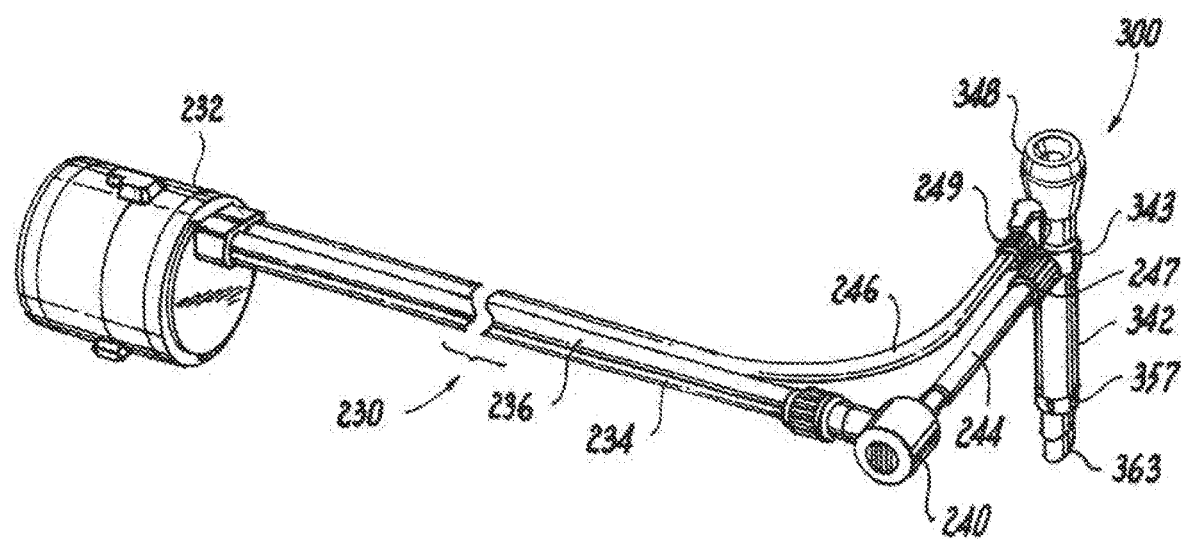
FIG. 20 is a perspective view of the filtered tube set of FIG. 14 in conjunction with the surgical access assembly of FIG. 18.
Figure 21:
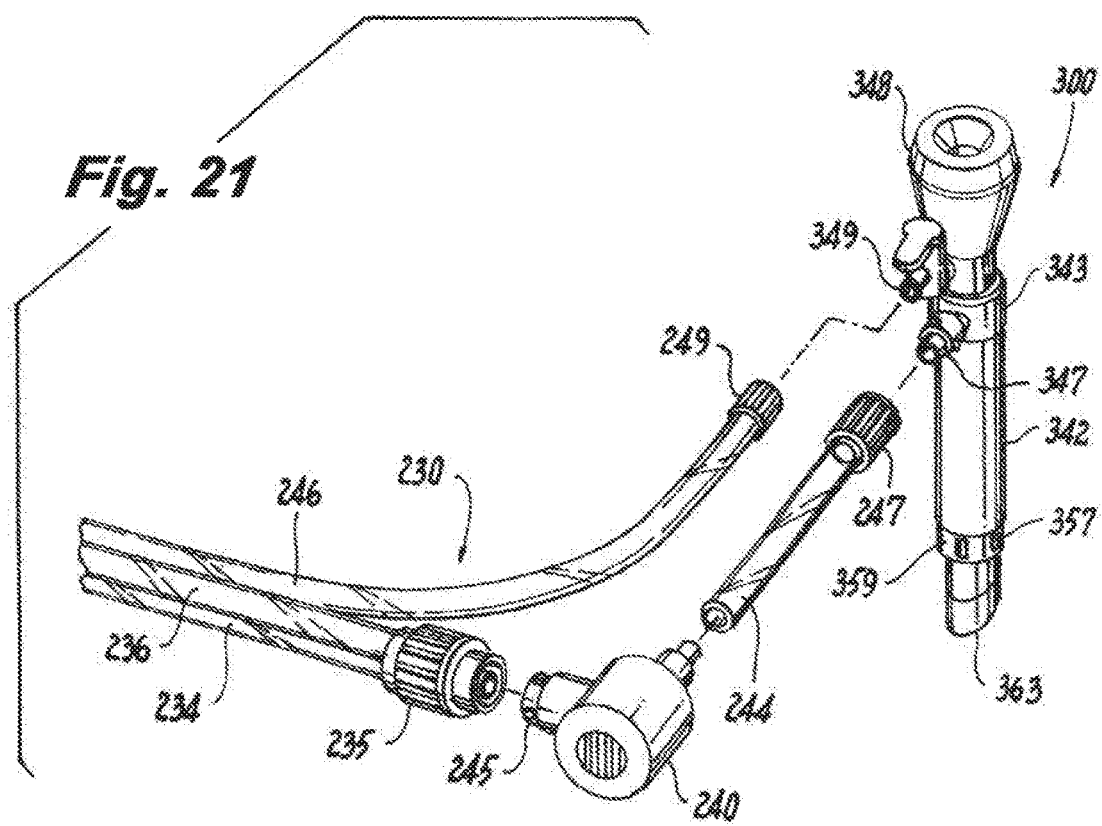
FIG. 21 is an exploded perspective view of the filtered tube set shown in FIG. 20, with parts separated for ease of illustration.

More particularly, the gas delivery lumen 234 and the gas return lumen 236 are operatively associated with a rotatable dual lumen concentric connector 235 that mates with a correspondingly configured fitting 245 extending from the housing 250 of gaseous sealing module 240, in a direction perpendicular to the connection for the gas sealed lumen 244, as best seen in FIG. 15*a*. A connector of this type is disclosed in commonly assigned U.S. Patent Application Publication No. 2017/0361084, the disclosure of which is herein incorporated by reference in its entirety. The housing 250 of gaseous sealing module 240 further includes a louvered vent 280 that facilitates bi-directional gas exchange with atmosphere (i.e., for air entrainment and over pressure relief by way of lumen 244) and it is arranged in-line with the gas sealed lumen 244, as best seen in FIGS. 16 and 17.

In this embodiment of the invention, the gaseous sealing module 240 includes the two-part ring jet assembly 290 of the type shown in FIG. 13 and described in commonly assigned U.S. Pat. No. 9,907,569, for generating a gaseous seal with the interior region 285 of the throat portion 284 of housing 250, which creates a stable pressure barrier that maintains stable pressure through the length of the gas sealed lumen 244 to the access port 242 so as to maintain a stable pressure and facilitate smoke evacuation within the surgical cavity 18 of a patient 20 during an endoscopic surgical procedure.

Figure 14:
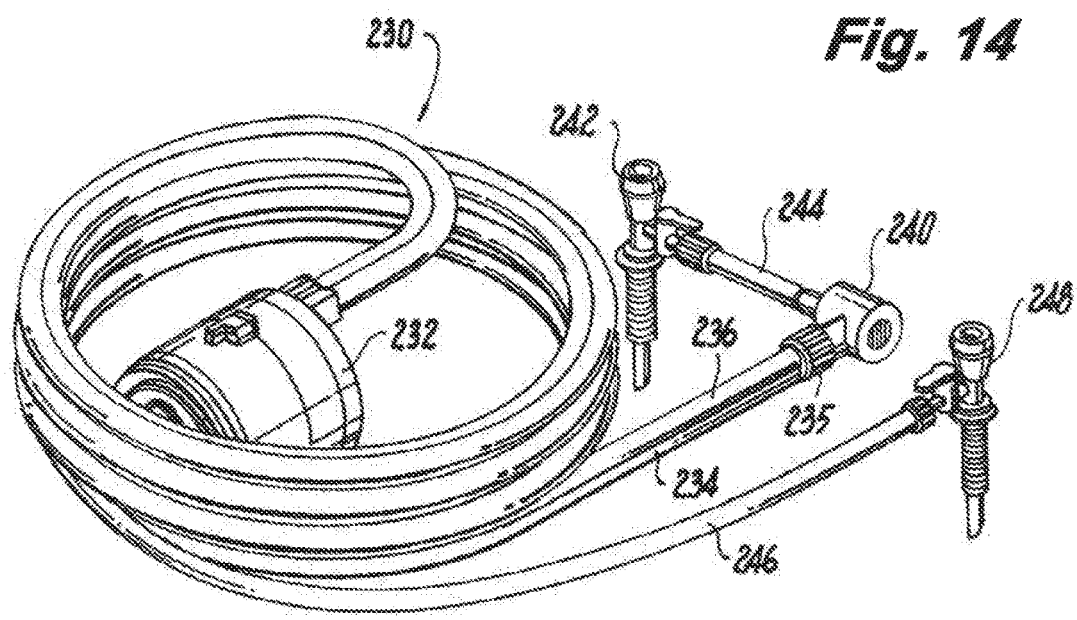
FIG. 14 is an illustration of another embodiment of a filtered tube set for use with the gas delivery device shown in FIG. 1, which includes gas delivery and return lines extending between a filter cartridge configured for reception in the gas delivery device, a remote gaseous sealing module, a valve sealed access port communicating with the gas sealed lumen attached to the gaseous sealing module and an insufflation and sensing lumen communicating with another valve sealed access port.

Referring now to FIGS. 18 through 23, there is illustrated a surgical access assembly 300 that is adapted and configured for use in conjunction with any one of the previously described filtered tube sets, such as for example, the filtered tube set 230 shown in FIG. 14. The surgical access assembly 300 primarily includes a tubular gas sealed sleeve 342 and a valve sealed access port 348. The tubular gas sealed sleeve 342 has a proximal end portion 343 that includes a fitting 347 for communication with a connector 247 on the distal end portion of the gas sealed lumen 244 of tube set 230. The valve sealed access port 348 is configured for coaxial installation within the tubular sleeve 342 to provide mechanically sealed instrument access to the surgical cavity 18 and it has a fitting 349 for communicating with a connector 249 on the distal end of the insufflation and sensing lumen 246 of tube set 230.

As best seen in FIGS. 22 and 23, the access port 348 has a proximal housing 365 that houses a duckbill seal 367 for providing sealed access to the surgical cavity 18 through the central lumen 369 of the access port 348. With specific reference to FIG. 22, the central lumen 369 provides an insufflation and sensing path for the system 300, and elongated annular channel 353 is formed between an inner peripheral surface of the gas sealed sleeve 342 and an outer peripheral surface of the access port 348 so that the gas sealed lumen 244 is in communication with the surgical cavity 18 to maintain a stable pressure and facilitate smoke evacuation within the surgical cavity 18.

A sealing ring 355 is associated with the proximal end portion 343 of the sleeve 342 for sealing a proximal end of the annular channel 353, and a plurality of circumferentially spaced apart flow channels 357 are formed in the distal end portion 359 of the gas sealed sleeve 342 to facilitate communication between the annular channel 353 and the surgical cavity of a patient, as best seen in FIG. 23, thereby maintaining a stable pressure within the surgical cavity and facilitate smoke evacuation during an endoscopic surgical procedure.

In use, to access the surgical cavity 18 with the access assembly 300 during an endoscopic surgical procedure, the valve sealed port 348 is first installed into the gas sealed sleeve 342, and then the gas sealed sleeve 342 together with the valve sealed port 348 are introduced into the surgical cavity 18 of the patient 20. The angled distal edge 363 of the valve sealed port 348 aids in the percutaneous introduction of the assembly 300, which would be accomplished using a typical obturator or introducer placed therein, as is well known in the art.

The method further includes the steps of connecting the fitting 247 on the end of the gas sealed lumen 244 to the fitting 347 of the sleeve 342, which is adapted for bi-directional gas flow to and from the gas sealed sleeve 342, and the step of connecting the fitting 249 on the end of the insufflation and sensing lumen 246 to the fitting 349 of the valve sealed port 348. In the event that a metallic access device is used in this system, it is envisioned that the sleeve 342 would need to be grounded to prevent an electrical shock resulting from capacitive coupling.

Figure 24:
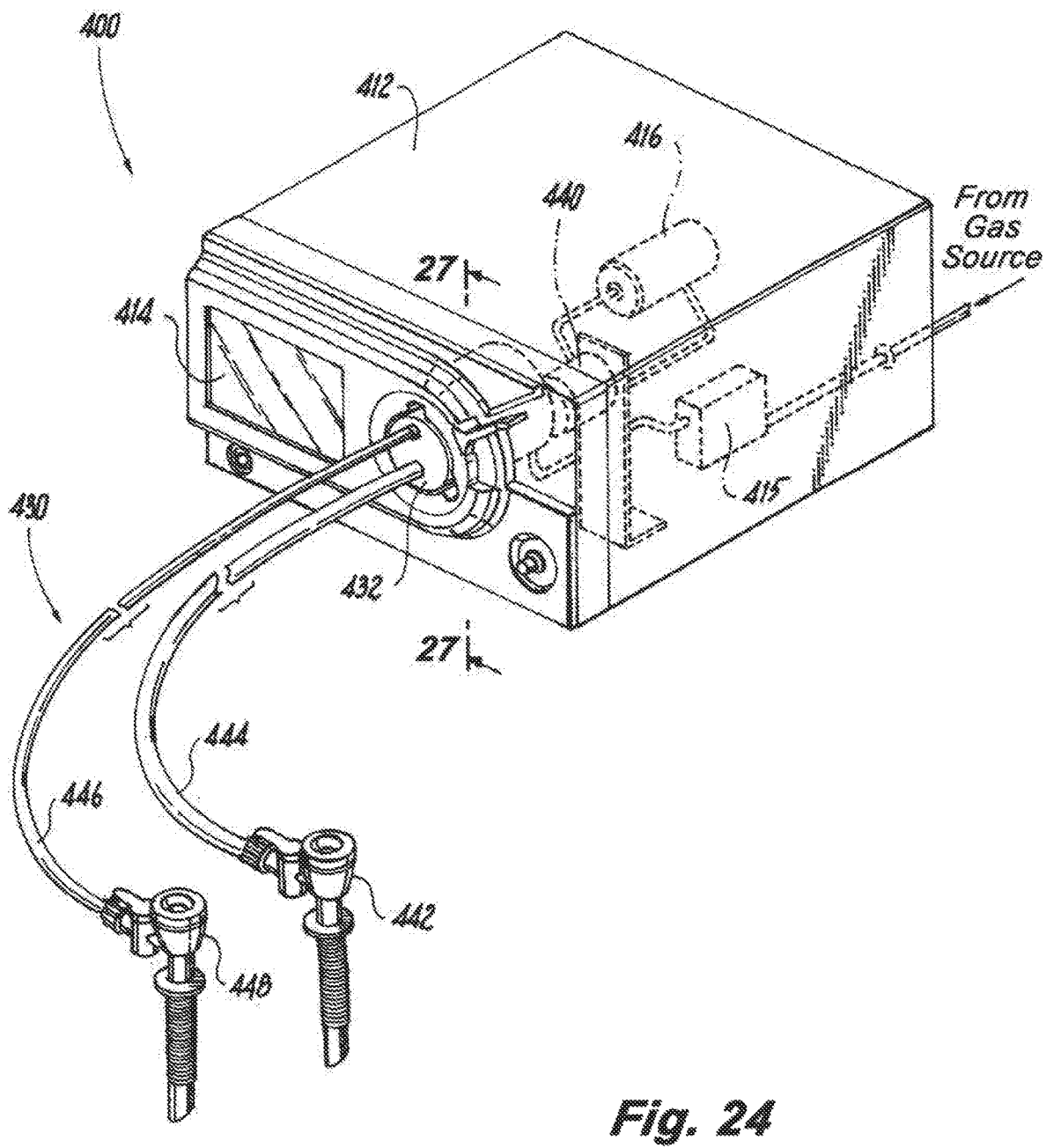
FIG. 24 is an illustration of another gas delivery system constructed in accordance with a preferred embodiment of the subject invention wherein the gas delivery device includes an internal gaseous sealing module that communicates with a gas sealed lumen extending from a filter cartridge to a valve sealed access port, and which also includes an insufflation and sensing lumen extending from the filter cartridge to a second valve sealed access port.

Referring now to FIG. 24, there is illustrated a unique gas delivery system 400 constructed in accordance with a preferred embodiment of the subject invention. Gas delivery system 400 includes a gas delivery device 412 that has an internal gaseous sealing module 440, as opposed to the external remotely located gaseous sealing modules described above. The gas delivery device 412 also includes a graphical user interface 414 for setting operating parameters, an internal insufflator 415 for receiving insufflation gas from a source and delivering that gas to the surgical cavity of the patient, and a pump 416 for facilitating the circulation/recirculation of pressurized gas relative to internal gaseous sealing module 440. The insufflator 415 and gaseous sealing module 440 communicates with a unique filtered tube set 430, which is best seen in FIG. 25.

Figure 25:
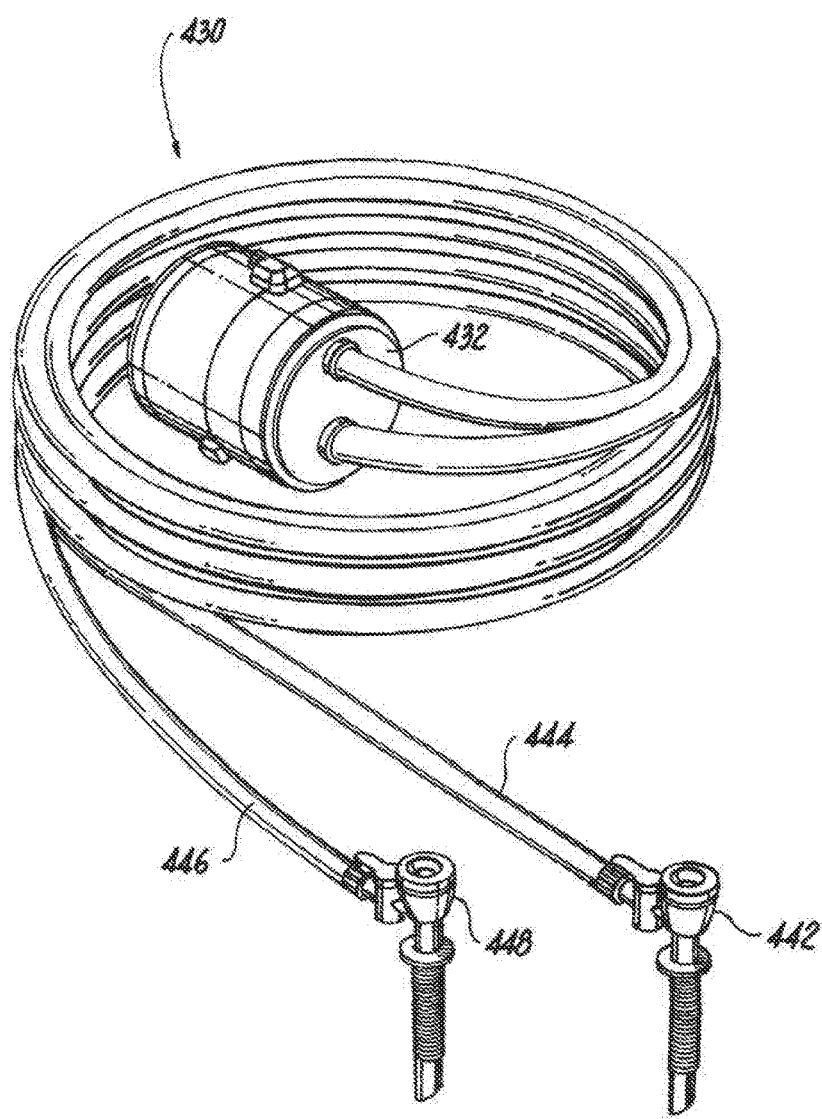
FIG. 25 is a perspective view of the filtered tube set employed with the gas delivery device of FIG. 24, with the valve sealed access ports associated therewith.

Referring to FIG. 25, the filtered tube set 430 includes a filter cartridge 432 from which extends a gas sealed lumen 444 and an insufflation and sensing lumen 446. The gas sealed lumen 444 extends from the filter cartridge 432 to a first valve sealed access port 442, and the insufflation and sensing lumen 446 extends to a second valve sealed access port 448. The internal gaseous sealing module 440 generates a gaseous seal that creates a stable pressure barrier that maintains stable pressure through the gas sealed lumen 444 to the first access port 442 to maintain a stable pressure and facilitates smoke evacuation within the surgical cavity of a patient during an endoscopic surgical procedure.

Figure 26:
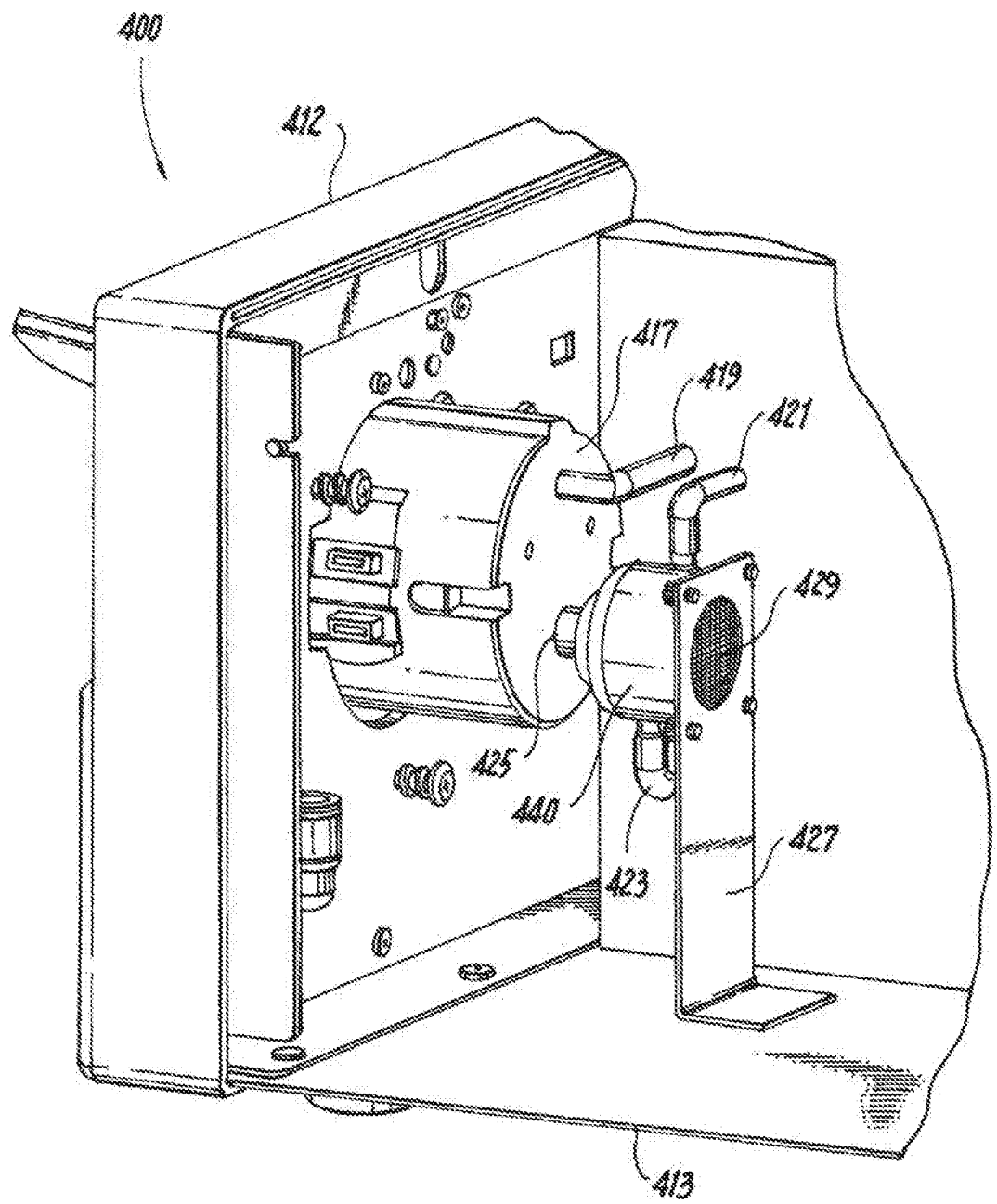
FIG. 26 is a localized perspective view of the interior of the gas delivery device shown in FIG. 24.
Figure 27:
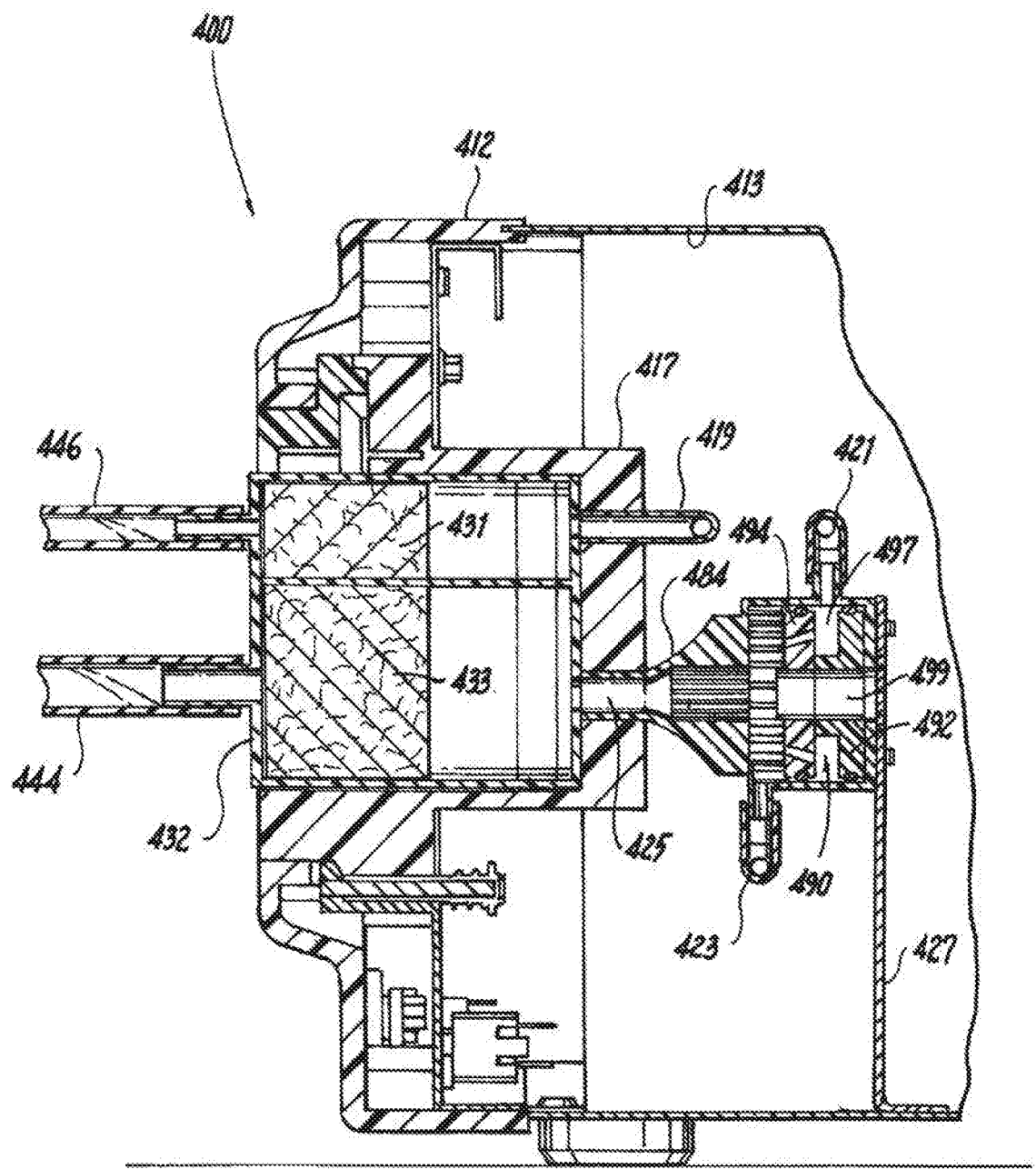
FIG. 27 is a cross-sectional view taken along line 27-27 of FIG. 24.
Figure 29:
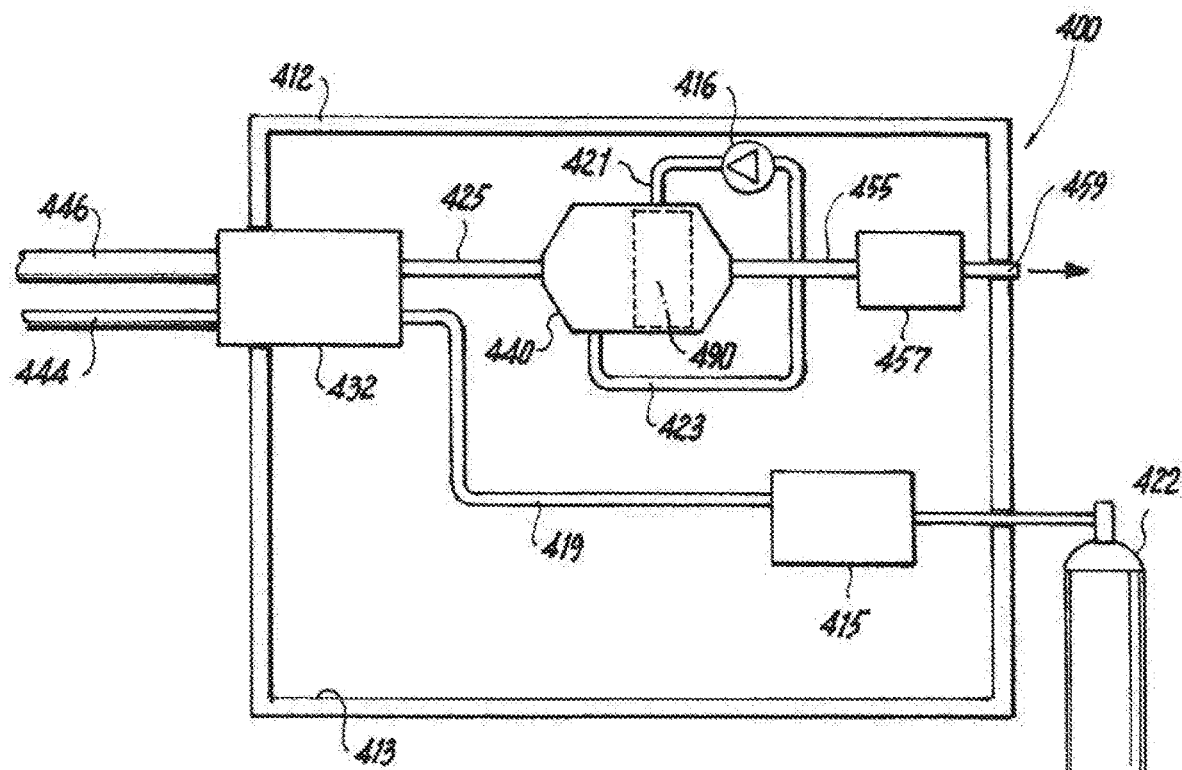
FIG. 29 is a schematic representation of the gas delivery device of FIG. 24, illustrating the gas flow paths associated therewith.

Referring to FIGS. 26 through 27 in conjunction with the schematic diagram of FIG. 29, there is illustrated the interior of the housing 413 of the gas delivery device 412, which includes a reception cavity 417 for releasably receiving the cartridge 432 of the filtered tube set 430, which communicates with the internal gaseous sealing module 440 by way of an internal gas sealed tube 425. The filter cartridge 432 includes a first filter element 431 for filtering insufflation gas flow to the insufflation conduit 446 and a second filter element 433 for filtering gas flowing to and from the gas sealed lumen 444. While the filter cartridge 432 has been described as being part of the replaceable and disposable tube set 430, it is envisioned and well within the scope of the subject disclosure that one or both of the filter elements 431 and 433 could be in the form of a removable filter element installed in an interior compartment within the housing 413 of gas delivery device 412, as shown for example in FIG. 29 (see, e.g., internal filter 457).

An internal insufflation tube 419 extends between the insufflator 415 and the reception cavity 417. In addition, an internal gas delivery conduit 421 extends from high pressure outlet side of the pump 416 to the inlet side of the gaseous sealing module 440 and an internal gas return conduit 423 extends between the outlet side of the gaseous sealing module 440 and the inlet or suction side of the pump 416.

Figure 28:
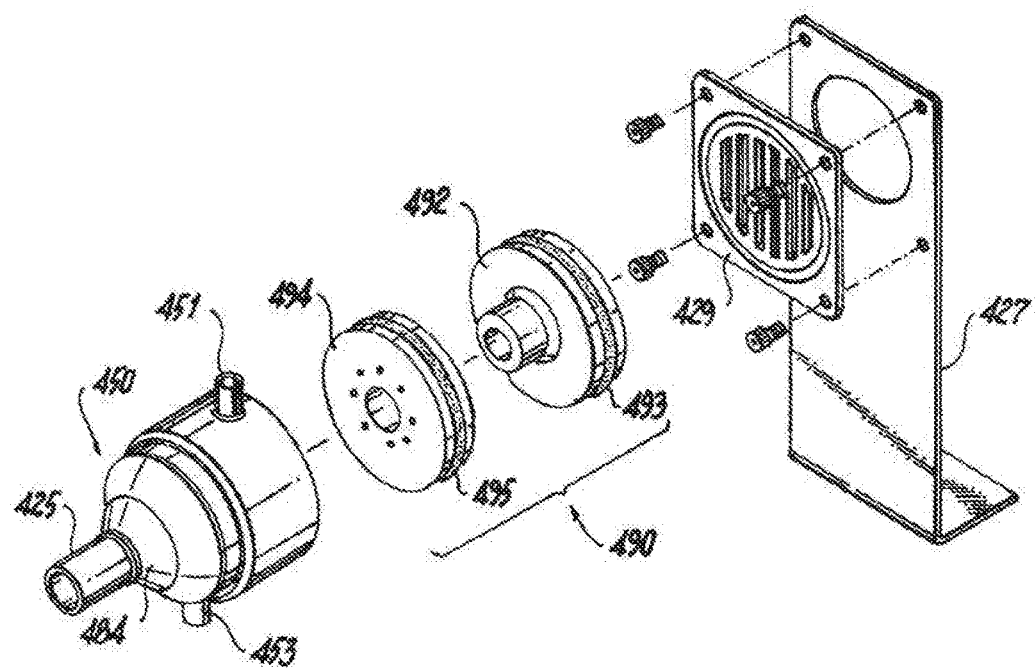
FIG. 28 is an exploded perspective view of the internal gaseous sealing module located within the gas delivery device shown in FIG. 24, with parts separated for ease of illustration.

Referring to FIG. 26 in conjunction with FIG. 28, the gaseous sealing module 440 is supported with the housing 413 of the gas delivery device 412 on an upstanding bracket 427 that includes a louvered vent plate 429 for accommodating gas exchange, including but not limited to, air entrainment from atmosphere into the gaseous sealing module 440 and gas release to atmosphere from the gaseous sealing module 440. As illustrated in FIG. 29, an embodiment of the gas delivery device 412 includes an internal vent tube 455 that extends from the housing 450 of the gaseous sealing module 440 to an internal filter element 457. The internal filter 457 communicates with an outlet tube 459 that extends from the housing 413 to atmosphere to facilitate gas exchange.

The housing 450 of the gaseous sealing module 440 is dimensioned and configured to support a pressurized nozzle assembly 490, which is adapted and configured to accelerate pressurized gas to generate a gaseous seal within the throat section 484 that extends from the housing 450 to the gas sealed tube 425. The nozzle assembly 490 includes an upper ring component 492 having an associated O-ring seal 493 and a lower nozzle disk 494 having an associated O-ring seal 495. As explained in more detail below, the nozzle disc 494 includes one or more gas accelerating nozzles.

As best seen in FIG. 27, a gas inlet plenum 497 is formed between the lower surface of upper ring component 492 and the upper surface of the lower nozzle disk 494 for receiving pressurized gas from the internal gas delivery conduit 421. More particularly, the housing 450 includes an inlet port 451 for communicating with the gas delivery conduit 421 and an outlet port 453 for communicating with the gas return conduit 423. The nozzle assembly 490 defines a vent path 499 to facilitate bi-directional gas exchange with atmosphere, by way of the relief by way of louvered vent plate 429.

Referring now to FIGS. 30-37, there are illustrated four different embodiments of a metallic nozzle disc, each of which is adapted and configured to generate a gaseous seal within the internal gaseous sealing module 440 shown in FIG. 28, as explained above. In these embodiments, each metallic disk is 594 is formed with at least one radially inwardly angled nozzle 596 formed therein for accelerating pressurized gas received from the pump 416 to generate the gaseous seal in the internal gaseous sealing module 444 of gas delivery device 412, a cylindrical bore 598 for accommodating air entrainment into and gas release from the gas sealed lumen 444, and an O-ring seal 595 for sealing isolating the high and low pressure sides of the disk 594 within the housing 450 of module 440.

Figure 30:
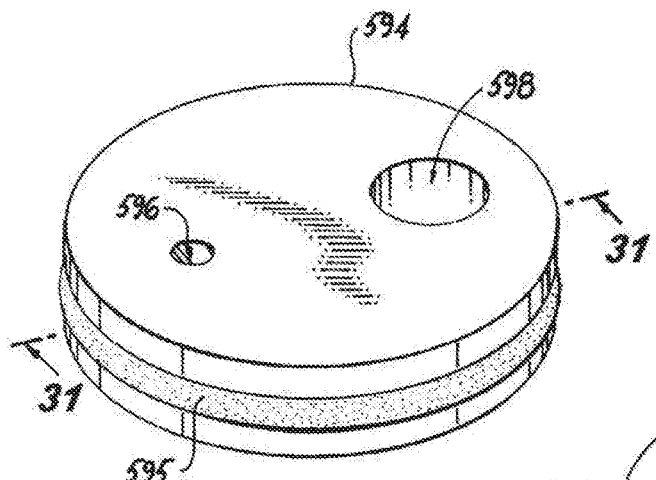
FIGS. 30-37 depict four different embodiments of a one piece nozzle disc for generating a gaseous seal with the internal gaseous sealing module shown in FIG. 28.
Figure 31:
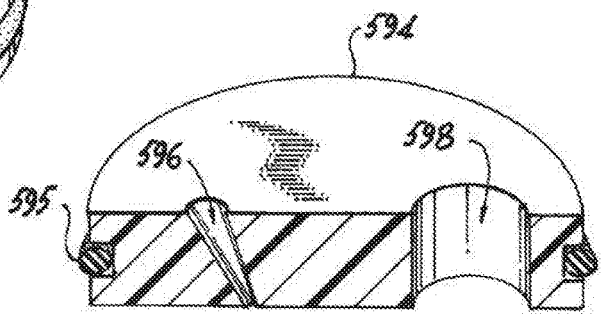
Figure 32:
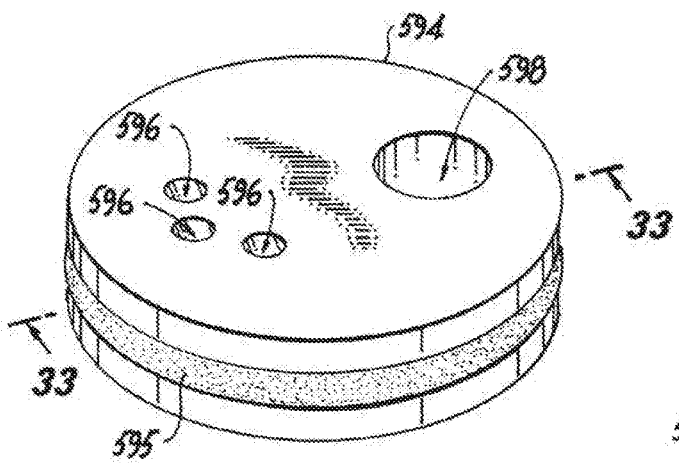
Figure 33:
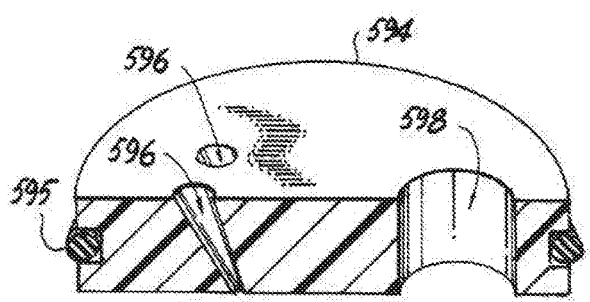

Referring first to FIGS. 30 and 31, an embodiment of the disk 594 includes one radially inwardly angled nozzle 596 radially spaced apart from the cylindrical bore 598, both of which are offset from a central axis of the disk 594. An alternative embodiment of the disk 594, has a plurality of radially inwardly angled nozzles 596 formed therein, which are radially spaced apart from the cylindrical bore 598, which are all offset from a central axis of the disk, as illustrated in FIGS. 32 and 33.

Figure 34:
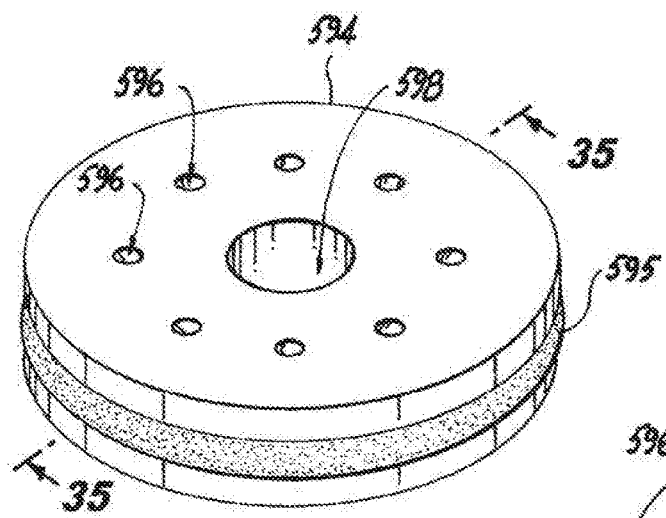
Figure 35:
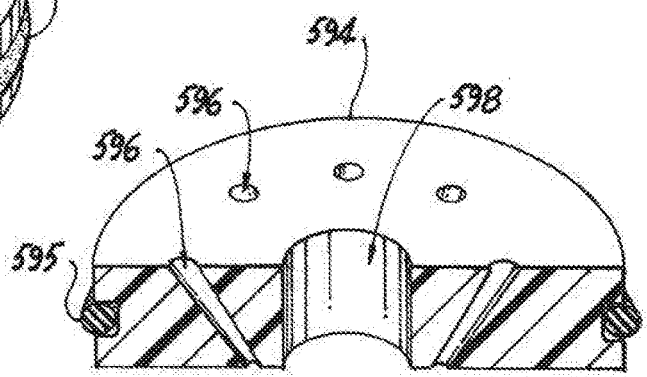
Figure 36:
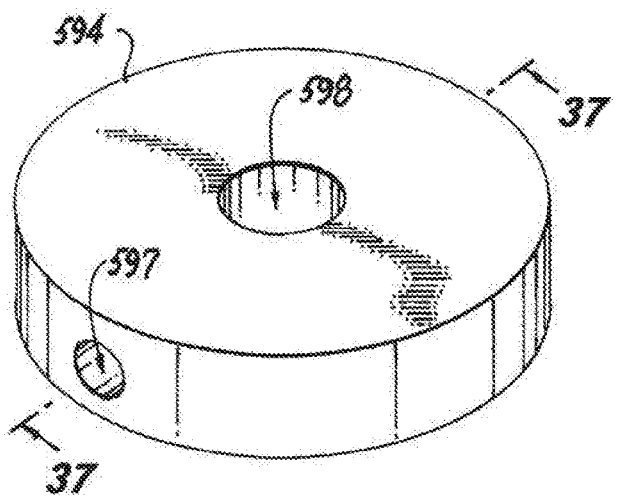
Figure 37:
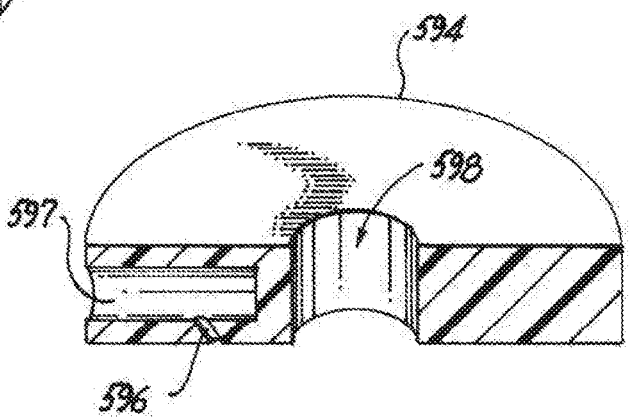

In another embodiment, the disk 594 has a plurality of radially inwardly angled jet nozzles 596 formed therein, which surround the cylindrical bore 598, which is axially aligned with a central axis of the disk 594, as illustrated in FIGS. 34 and 35. In yet another embodiment of the disk 594, there is one radially inwardly angled nozzle 596 that receives pressurized gas through a radial inlet passage 597 extending from an outer periphery of the disk 594, and the cylindrical bore 598 is axially aligned with a central axis of the disk 594, as illustrated in FIGS. 36 and 37.

In essence, the cylindrical bore 598 in each of these metallic discs 594 provides the same functionality as the central bore of a ring jet assembly for a gas sealed access port (see U.S. Pat. No. 8,795,223), which is centrally located to allow instrument passage. However, since the jet discs 594 are internal to the gas delivery device 412, and they do not need to accommodate instrument passage, the cylindrical bore 598 in each disk 594 does not need to be as large and it can be located off-center. This is because a pneumatic seal does not need to be formed around a cylindrical instrument passing through the access port. While this bore is cylindrical for ease of manufacture, it need not be.

While the subject disclosure has been shown and described with reference to preferred embodiments, those skilled in the art will readily appreciate that changes or modifications may be made without departing from the scope of the subject disclosure.

What is claimed is:

1. A system for performing an endoscopic surgical procedure in a body cavity, comprising:
    a) a gas delivery device having a pump for delivering pressurized gas to a gas delivery lumen extending therefrom and having an insufflator for delivering insufflation gas to an insufflation lumen extending therefrom;
    b) a gaseous sealing module communicating with a distal end of the gas delivery lumen, external to the gas delivery device, the gaseous sealing module including a housing containing a jet assembly for receiving pressurized gas from the gas delivery lumen, wherein the jet assembly is adapted and configured to accelerate the pressurized gas to generate a gaseous seal within an interior region of the housing, which maintains a stable pressure throughout a gas sealed lumen extending therefrom as a result of the gaseous seal, and wherein the jet assembly includes an upper ring jet member and a lower ring jet member;
    c) a gas sealed sleeve having a proximal end portion communicating with a distal end of the gas sealed lumen, the gas sealed sleeve defining an inner tubular surface having a sealing ring associated with a proximal end thereof; and
    d) a tubular access port configured for coaxial installation within the gas sealed sleeve and having a proximal housing containing a duckbill seal providing sealed instrument access to the body cavity through a central lumen formed therein and communicating with a distal end of the insufflation lumen, wherein an annular channel is formed between the inner tubular surface of the gas sealed sleeve and an outer tubular surface of the tubular access port, enclosed at a proximal end thereof by the sealing ring, so that the gas sealed lumen is in communication with the body cavity through a distal end portion of the annular channel to maintain a stable pressure within the body cavity as a result of the gaseous seal, wherein the central lumen of the tubular access port provides an insufflation and sensing path for the system.

2. The system as recited in claim 1, wherein a plurality of circumferentially spaced apart flow channels are formed in a distal end portion of the gas sealed sleeve to facilitate communication between the distal end portion of the annular channel and the body cavity.

3. The system as recited in claim 1, further comprising a gas return lumen extending from the gaseous sealing module back to the pump in the gas delivery device.

4. The system as recited in claim 3, wherein the gas delivery lumen and the gas return lumen communicate with a filter assembly that is dimensioned and configured for reception within the gas delivery device.

5. The system as recited in claim 1, wherein the housing of the gaseous sealing module is a vented housing for facilitating air entrainment from atmosphere into the body cavity and gas release to atmosphere from the body cavity.

6. The system as recited in claim 1, wherein gas spent generating the gaseous seal is sent through a gas return lumen back to the gas delivery device.

7. A method of accessing a surgical cavity of a patient comprising the steps of:
    a) providing a gas sealed sleeve defining an inner tubular surface having a sealing ring associated with a proximal end thereof;
    b) installing a valve sealed trocar having a tubular body and a proximal housing containing a seal into the gas sealed sleeve so that an annular channel is formed between the inner tubular surface of the gas sealed sleeve and an outer surface of the tubular body of the valve sealed trocar, with the sealing ring enclosing a proximal end of the annular channel, wherein the valve sealed trocar has a central lumen formed therein providing an insufflation and sensing path;
    c) percutaneously introducing the gas sealed sleeve together with the installed valve sealed trocar into the surgical cavity of the patient, wherein the valve sealed trocar has an angled distal edge for percutaneously introducing the gas sealed sleeve together with the installed valve sealed trocar into the surgical cavity of the patient;
    d) connecting a gas sealed lumen to the gas sealed sleeve; and
    e) connecting the gas sealed lumen to a gaseous sealing module containing a jet assembly, wherein the jet assembly is adapted and configured to accelerate pressurized gas supplied by a gas delivery device to generate a gaseous seal within an interior region of the gaseous sealing module, which maintains a stable pressure throughout the gas sealed lumen and the annular channel formed between the inner tubular surface of the gas sealed sleeve and the outer surface of the tubular body of the valve sealed trocar as a result of the gaseous seal.

8. The method according to claim 7, further comprising the step of connecting an insufflation and sensing lumen to the valve sealed trocar.

* * * * *